United States Patent
Farhangnia et al.

(10) Patent No.: US 9,126,020 B2
(45) Date of Patent: Sep. 8, 2015

(54) CATHETER APPARATUS WITH TELESCOPING LUMEN CATHETERS AND ITS USE IN METHODS FOR TREATING VASCULATURES

(71) Applicant: Roxwood Medical, Inc., Redwood City, CA (US)

(72) Inventors: Mehrdad Farhangnia, San Francisco, CA (US); Mark C. Yang, San Francisco, CA (US); Mark Taber, St. Louis, MO (US)

(73) Assignee: Roxwood Medical, Inc., Redwood City, CA (US)

( * ) Notice: Subject to any disclaimer, the term of this patent is extended or adjusted under 35 U.S.C. 154(b) by 0 days.

(21) Appl. No.: 13/842,744

(22) Filed: Mar. 15, 2013

(65) Prior Publication Data
US 2013/0253474 A1  Sep. 26, 2013

Related U.S. Application Data

(60) Continuation-in-part of application No. 13/166,623, filed on Jun. 22, 2011, now Pat. No. 8,764,730, which is a division of application No. 12/147,130, filed on Jun. 26, 2008, now Pat. No. 7,988,646.

(Continued)

(51) Int. Cl.
*A61M 25/09* (2006.01)
*A61M 25/00* (2006.01)
(Continued)

(52) U.S. Cl.
CPC ........... *A61M 25/09* (2013.01); *A61M 25/0071* (2013.01); *A61M 25/0074* (2013.01);
(Continued)

(58) Field of Classification Search
CPC ..................... A61M 25/0068; A61M 25/0074; A61M 25/0082; A61M 25/04; A61M 25/09041

USPC .......... 600/585; 604/510, 523, 526, 527, 528, 604/530, 532, 536
See application file for complete search history.

(56) References Cited

U.S. PATENT DOCUMENTS

| 4,854,325 | A | 8/1989 | Stevens |
| 4,894,051 | A | 1/1990 | Shiber |

(Continued)

FOREIGN PATENT DOCUMENTS

| EP | 0 592 726 B1 | 3/1997 |
| GB | 2472213 A | 2/2011 |

(Continued)

OTHER PUBLICATIONS

Non-Final Office Action issued in counterpart U.S. Appl. No. 13/166,623, dated Oct. 11, 2013, 18 pages.
PCT/US13/66217: International Search Report and Written Opinion mailed Jan. 16, 2014.
U.S. Appl. No. 12/147,130: Notice of Allowance dated Mar. 22, 2011.

(Continued)

*Primary Examiner* — Adam J Eiseman
(74) *Attorney, Agent, or Firm* — Michele V. Frank, Esq.; Venable LLP

(57) ABSTRACT

The invention provides for methods and catheter apparatus for passing one or more guidewires (via the use of one or more telescoping guidewire lumens) through a chronic total occlusion of a vasculature. The catheter apparatus may include: a catheter shaft having a distal end; one or more telescoping guidewire lumen catheters passing longitudinally through the shaft, wherein the one or more guidewire lumen catheters are capable of telescoping beyond the distal end of the catheter shaft; an expansible distal portion of the shaft; and a retractable sheath covering at least a portion of the expansible distal portion of the shaft, wherein retracting the retractable sheath from the expansible distal portion of the shaft directly activates the expansible distal portion of the shaft causing expansion of the expansible distal portion of the shaft.

19 Claims, 29 Drawing Sheets

Related U.S. Application Data

(60) Provisional application No. 60/929,395, filed on Jun. 26, 2007, provisional application No. 60/960,900, filed on Oct. 19, 2007, provisional application No. 60/996,057, filed on Oct. 26, 2007, provisional application No. 61/064,715, filed on Mar. 21, 2008, provisional application No. 61/716,856, filed on Oct. 22, 2012.

(51) Int. Cl.
  *A61M 25/01* (2006.01)
  *A61M 25/04* (2006.01)
  *A61M 25/10* (2013.01)
  *A61M 25/06* (2006.01)

(52) U.S. Cl.
  CPC .............. *A61M25/01* (2013.01); *A61M 25/04* (2013.01); *A61M 25/1002* (2013.01); *A61M 25/1011* (2013.01); *A61M 25/008* (2013.01); *A61M 25/0026* (2013.01); *A61M 25/0068* (2013.01); *A61M 2025/0046* (2013.01); *A61M 2025/0681* (2013.01); *A61M 2025/1045* (2013.01)

(56) References Cited

U.S. PATENT DOCUMENTS

| | | | |
|---|---|---|---|
| 4,917,094 A | 4/1990 | Lynch et al. | |
| 4,983,165 A | 1/1991 | Loiterman | |
| 5,334,166 A | 8/1994 | Palestrant | |
| 5,456,667 A | 10/1995 | Ham et al. | |
| 5,480,423 A | 1/1996 | Ravenscroft et al. | |
| 5,484,407 A | 1/1996 | Osypka | |
| 5,514,073 A | 5/1996 | Miyata et al. | |
| 5,575,771 A | 11/1996 | Walinsky | |
| 5,628,761 A | 5/1997 | Rizik | |
| 5,824,055 A | 10/1998 | Spiridigliozzi et al. | |
| 5,824,058 A | 10/1998 | Ravenscroft et al. | |
| 5,908,405 A | 6/1999 | Imran et al. | |
| 6,059,812 A | 5/2000 | Clerc et al. | |
| 6,071,285 A | 6/2000 | Lashinski et al. | |
| 6,126,649 A | 10/2000 | VanTassel et al. | |
| 6,165,209 A | 12/2000 | Patterson et al. | |
| 6,221,006 B1 | 4/2001 | Dubrul et al. | |
| 6,251,132 B1 | 6/2001 | Ravenscroft et al. | |
| 6,371,978 B1 | 4/2002 | Wilson | |
| 6,398,708 B1 | 6/2002 | Hastings et al. | |
| 6,416,523 B1 | 7/2002 | Lafontaine | |
| 6,425,898 B1 | 7/2002 | Wilson et al. | |
| 6,454,775 B1 | 9/2002 | Demarais et al. | |
| 6,544,253 B1 | 4/2003 | Tanner | |
| 6,596,005 B1 | 7/2003 | Kanz et al. | |
| 6,695,858 B1 | 2/2004 | Dubrul et al. | |
| 6,808,531 B2 | 10/2004 | Lafontaine et al. | |
| 6,835,203 B1 | 12/2004 | Vardi et al. | |
| 6,989,071 B2 | 1/2006 | Kocur et al. | |
| 7,037,320 B2 | 5/2006 | Brady et al. | |
| 7,131,981 B2 | 11/2006 | Appling et al. | |
| 7,144,364 B2 | 12/2006 | Barbut et al. | |
| 7,169,160 B1 | 1/2007 | Middleman et al. | |
| 7,396,358 B2 | 7/2008 | Appling et al. | |
| 7,485,139 B1 | 2/2009 | Ciamacco, Jr. | |
| 7,691,081 B2 | 4/2010 | Crossman | |
| 7,758,626 B2 | 7/2010 | Kim et al. | |
| 7,771,401 B2 | 8/2010 | Hekmat et al. | |
| 7,842,056 B2 | 11/2010 | Holman et al. | |
| 7,927,363 B2 | 4/2011 | Perouse | |
| 7,988,646 B2 | 8/2011 | Taber | |
| 8,066,757 B2 * | 11/2011 | Ferrera et al. | 623/1.12 |
| 8,070,761 B2 | 12/2011 | Weber et al. | |
| 8,100,935 B2 | 1/2012 | Rosenbluth et al. | |
| 8,152,951 B2 | 4/2012 | Zawacki et al. | |
| 8,162,964 B2 | 4/2012 | Piippo et al. | |
| 8,764,730 B2 | 7/2014 | Taber | |
| 2002/0010487 A1* | 1/2002 | Evans et al. | 606/180 |
| 2002/0116147 A1 | 8/2002 | Vock et al. | |
| 2003/0055445 A1 | 3/2003 | Evans et al. | |
| 2003/0078605 A1* | 4/2003 | Bashiri et al. | 606/159 |
| 2003/0163082 A1 | 8/2003 | Mertens | |
| 2003/0171765 A1 | 9/2003 | Kokate et al. | |
| 2003/0236533 A1 | 12/2003 | Wilson et al. | |
| 2004/0204738 A1 | 10/2004 | Weber et al. | |
| 2004/0215220 A1 | 10/2004 | Dolan et al. | |
| 2004/0220473 A1 | 11/2004 | Lualdi | |
| 2005/0085846 A1 | 4/2005 | Carrison et al. | |
| 2005/0216044 A1 | 9/2005 | Hong | |
| 2006/0069323 A1 | 3/2006 | Elkins et al. | |
| 2006/0069421 A1 | 3/2006 | Murray, III | |
| 2006/0149129 A1 | 7/2006 | Watts et al. | |
| 2006/0155366 A1 | 7/2006 | LaDuca et al. | |
| 2006/0190070 A1 | 8/2006 | Dieck et al. | |
| 2007/0010763 A1 | 1/2007 | Lentz et al. | |
| 2007/0083215 A1 | 4/2007 | Hamer et al. | |
| 2007/0135826 A1 | 6/2007 | Zaver et al. | |
| 2007/0233220 A1 | 10/2007 | Greenan | |
| 2007/0250035 A1 | 10/2007 | El-Nounou et al. | |
| 2008/0027529 A1 | 1/2008 | Hartley et al. | |
| 2008/0058839 A1 | 3/2008 | Nobles et al. | |
| 2009/0005757 A1 | 1/2009 | Taber | |
| 2009/0048577 A1 | 2/2009 | Gillies et al. | |
| 2010/0280450 A1 | 11/2010 | Jain | |
| 2010/0286465 A1 | 11/2010 | Benson | |
| 2010/0292614 A1 | 11/2010 | Delaney | |
| 2010/0331951 A1 | 12/2010 | Bei et al. | |
| 2011/0137163 A1 | 6/2011 | Eder | |
| 2011/0251591 A1 | 10/2011 | Taber | |
| 2011/0295234 A1 | 12/2011 | Eaton | |
| 2012/0046730 A1 | 2/2012 | von Oepen et al. | |
| 2012/0101561 A1 | 4/2012 | Porter | |
| 2012/0316600 A1 | 12/2012 | Ferrera et al. | |
| 2013/0253474 A1 | 9/2013 | Farhangnia et al. | |
| 2014/0128844 A1 | 5/2014 | Kornowski et al. | |
| 2014/0207179 A1 | 7/2014 | Farhangnia et al. | |
| 2014/0249511 A1 | 9/2014 | Taber | |
| 2014/0277008 A1 | 9/2014 | Farhangnia et al. | |

FOREIGN PATENT DOCUMENTS

| | | |
|---|---|---|
| JP | 2002-537943 A | 11/2002 |
| WO | 95/10317 A1 | 4/1995 |
| WO | WO-00/53120 A1 | 9/2000 |
| WO | 02/067772 | 9/2002 |
| WO | WO-2004/026180 A2 | 4/2004 |
| WO | WO-2007/062879 A1 | 6/2007 |
| WO | WO-2008-051898 A2 | 5/2008 |
| WO | WO-2009/003113 A1 | 12/2008 |
| WO | 2012/160562 A9 | 2/2013 |
| WO | 2014/066412 A1 | 5/2014 |

OTHER PUBLICATIONS

U.S. Appl. No. 13/166,623: Notice of Allowance dated Feb. 19, 2014.
U.S. Appl. No. 61/064,715, filed Jun. 26, 2007, Taber.
U.S. Appl. No. 60/996,057, filed Oct. 26, 2007, Taber.
U.S. Appl. No. 60/960,900, filed Oct. 19, 2007, Taber.
U.S. Appl. No. 60/929,395, filed Jun. 26, 2007, Taber.
International Search Report for PCT/US08/68380 dated Oct. 2, 2008.
European Search Report, issued in counterpart European Application No. 08772056, dated Mar. 29, 2012.
Non-Final Office Action issued in counterpart U.S. Appl. No. 12/147,130 dated Oct. 13, 2010, 10 pages.
PCT/US13/66217: International Preliminary Report on Patentability mailed Sep. 16, 2014.
U.S. Appl. No. 14/060,381: Office Action dated Oct. 24, 2014.
U.S. Appl. No. 14/223,458: Office Action dated Oct. 24, 2014.
PCT/US2015/021975: International Search Report and Written Opinion mailed Jun. 26, 2015.

\* cited by examiner

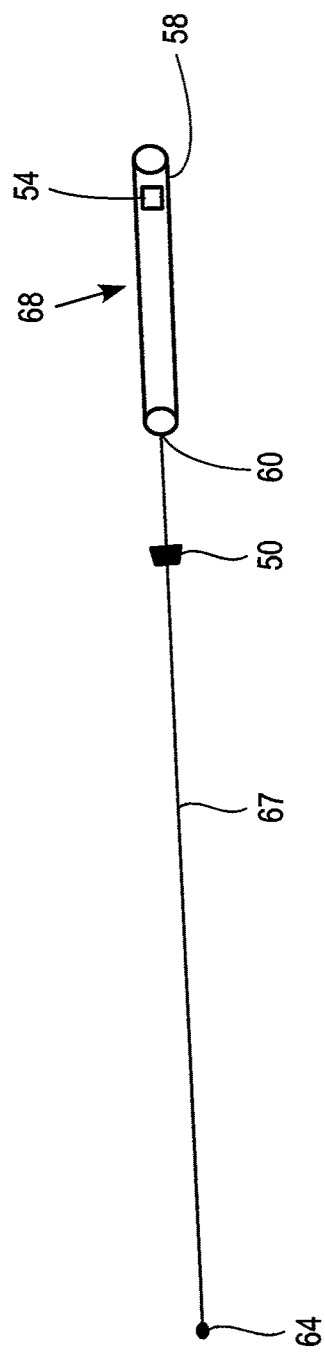
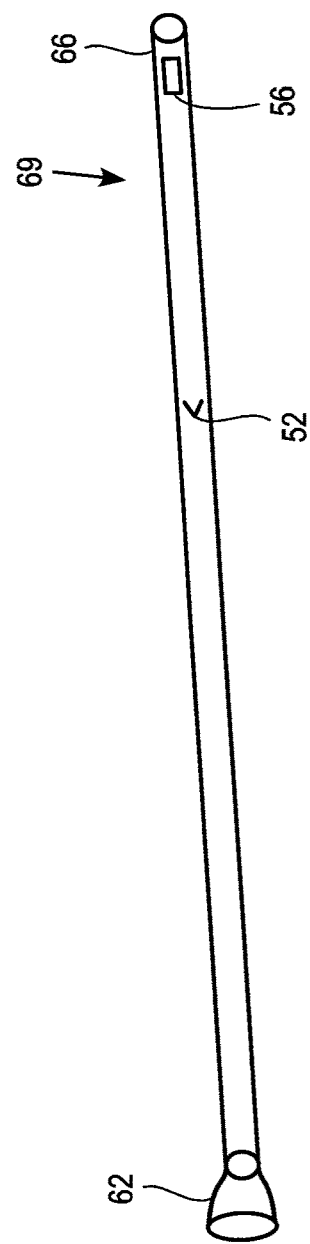
FIG. 1J
FIG. 1K

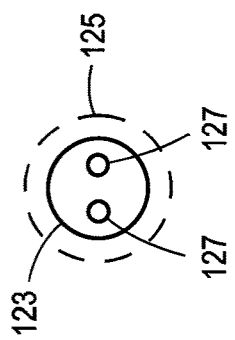
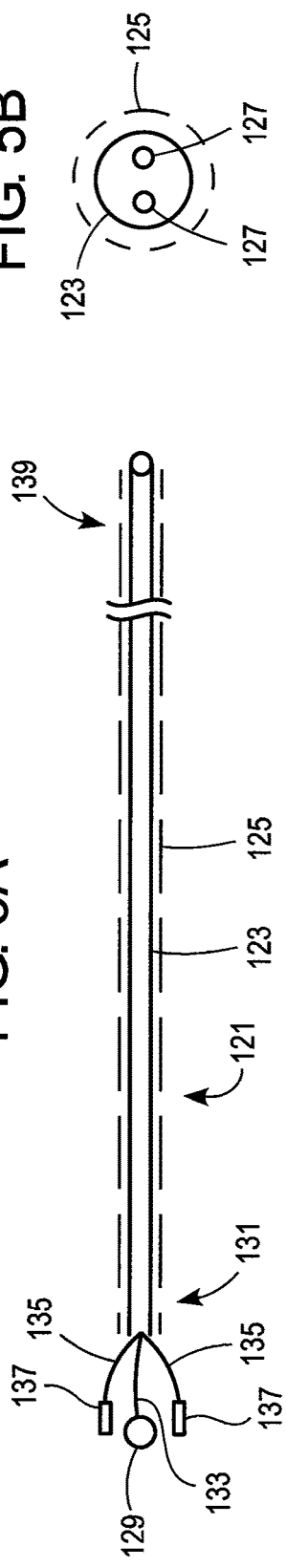
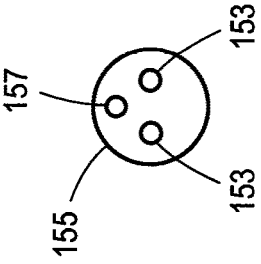
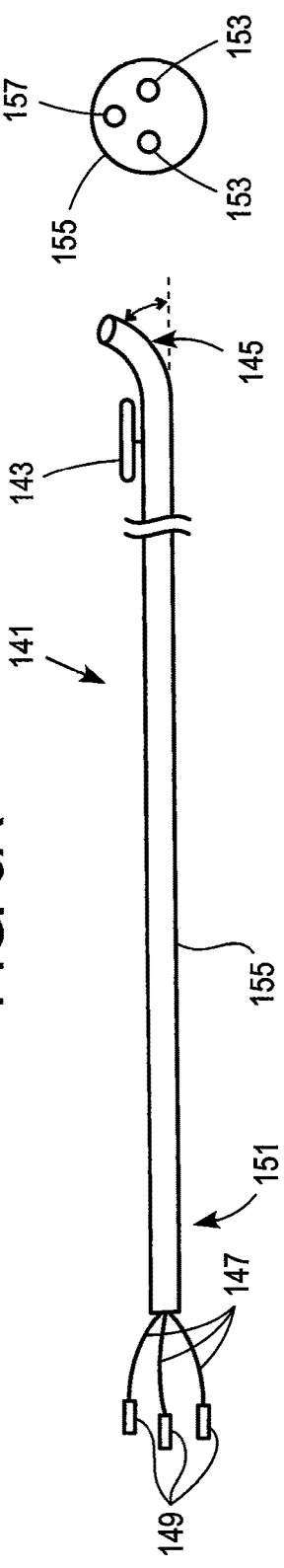

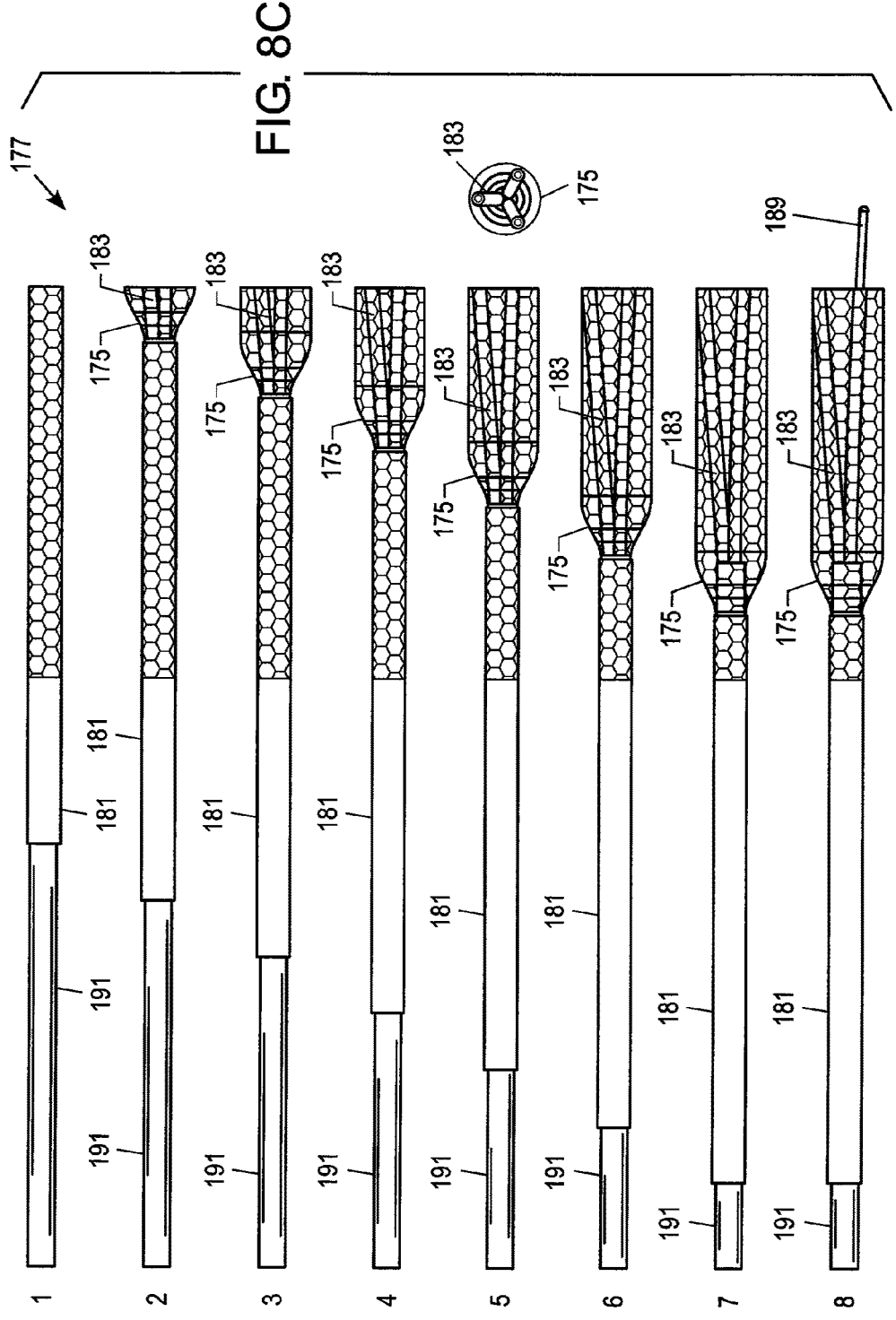

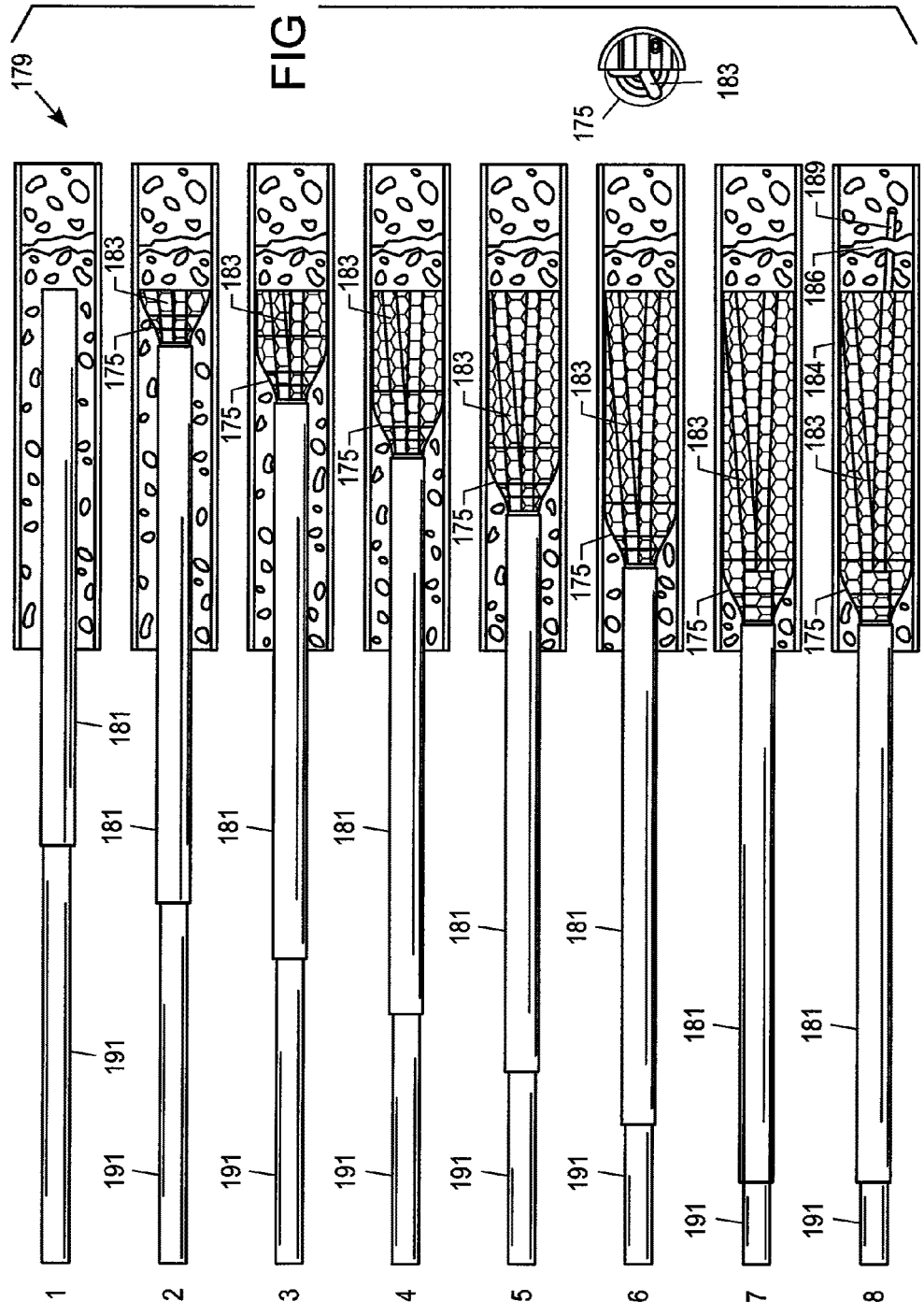

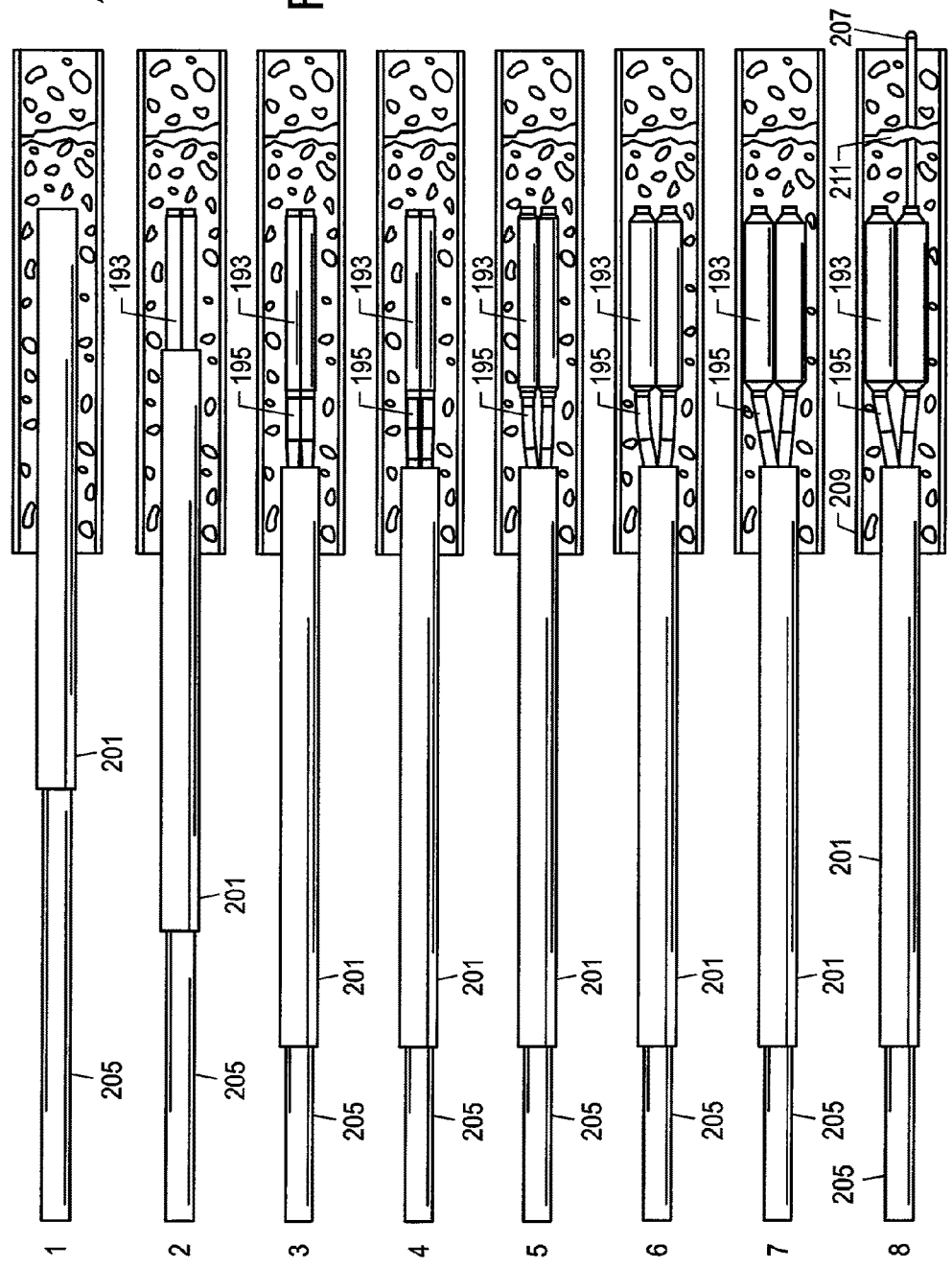

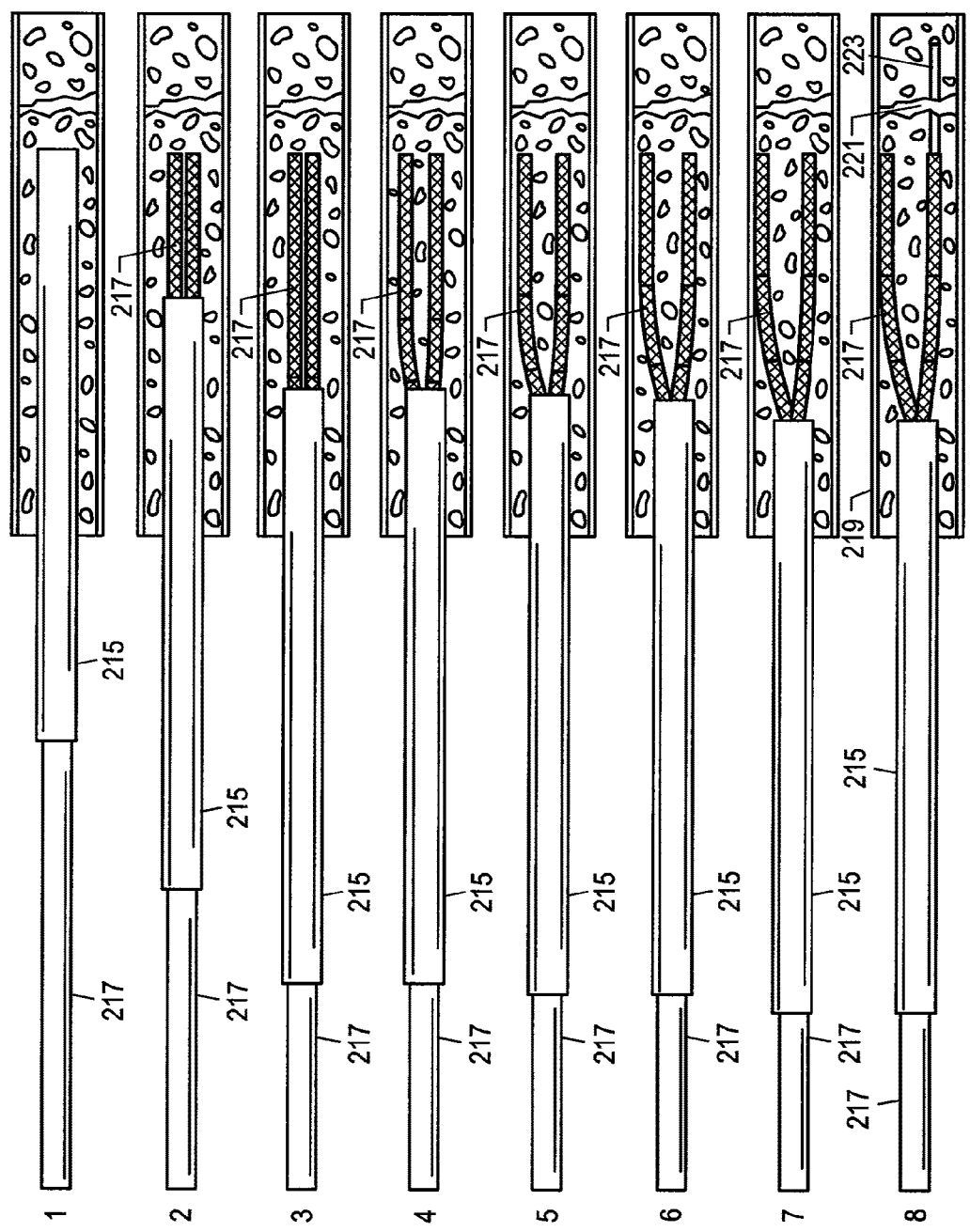

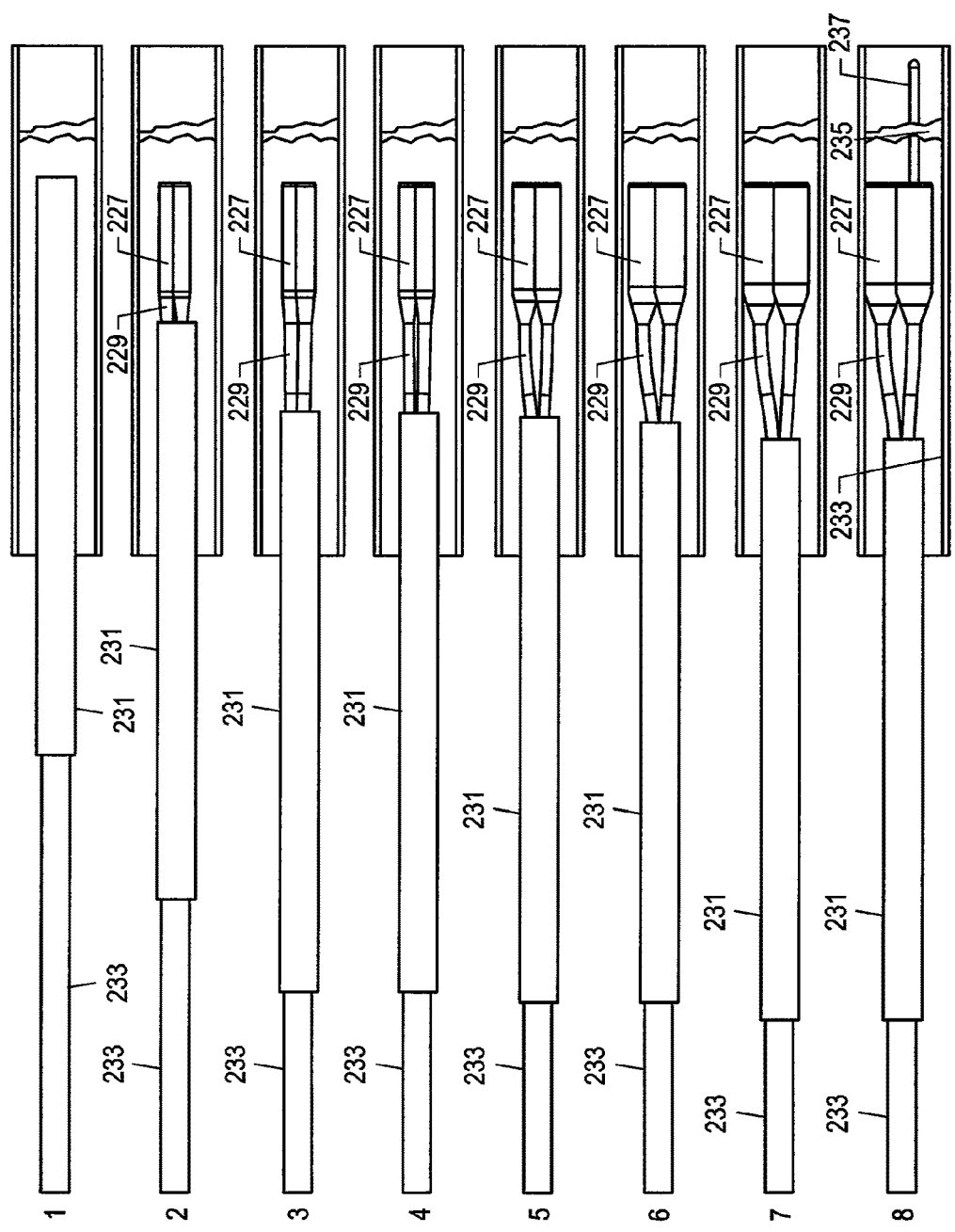

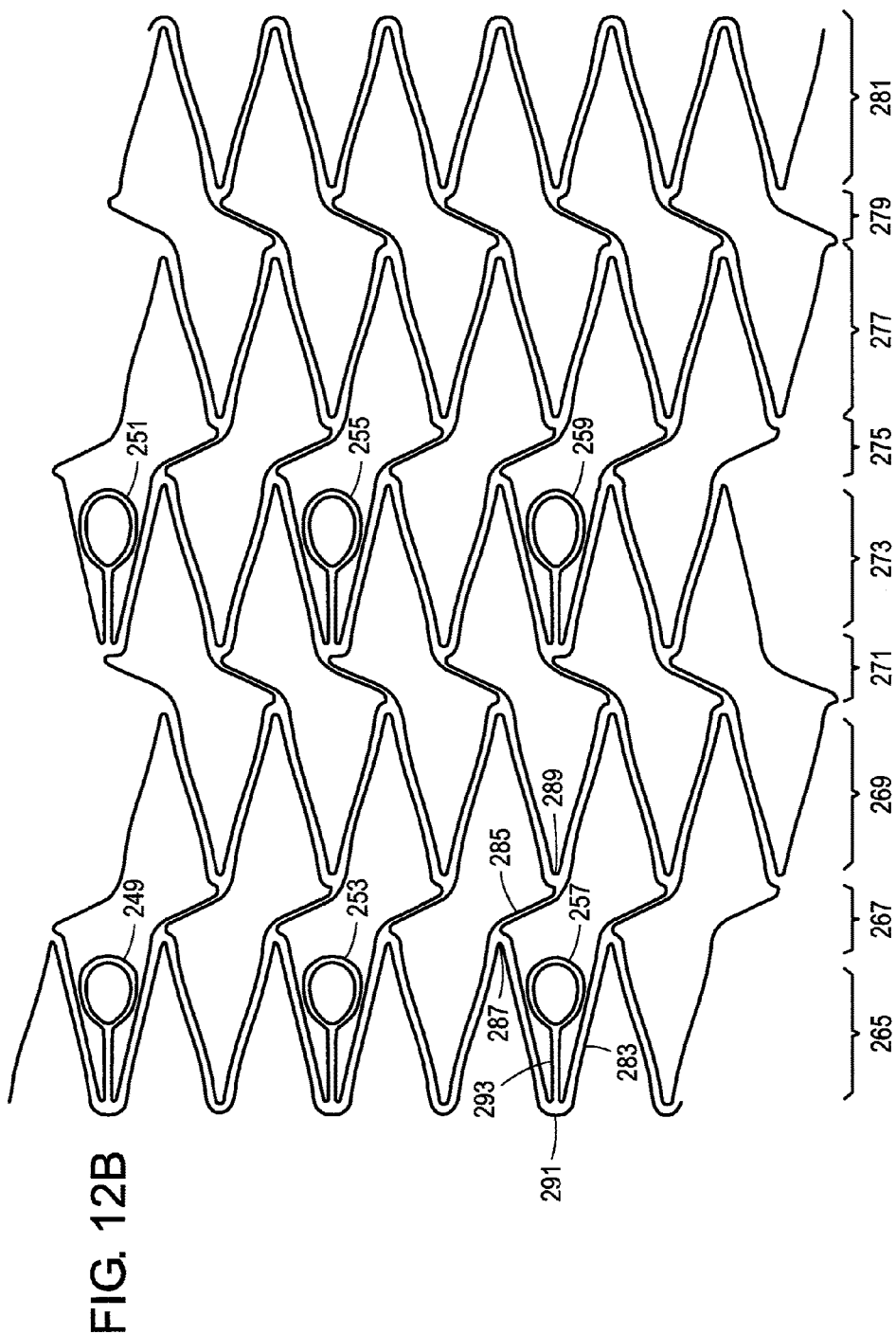

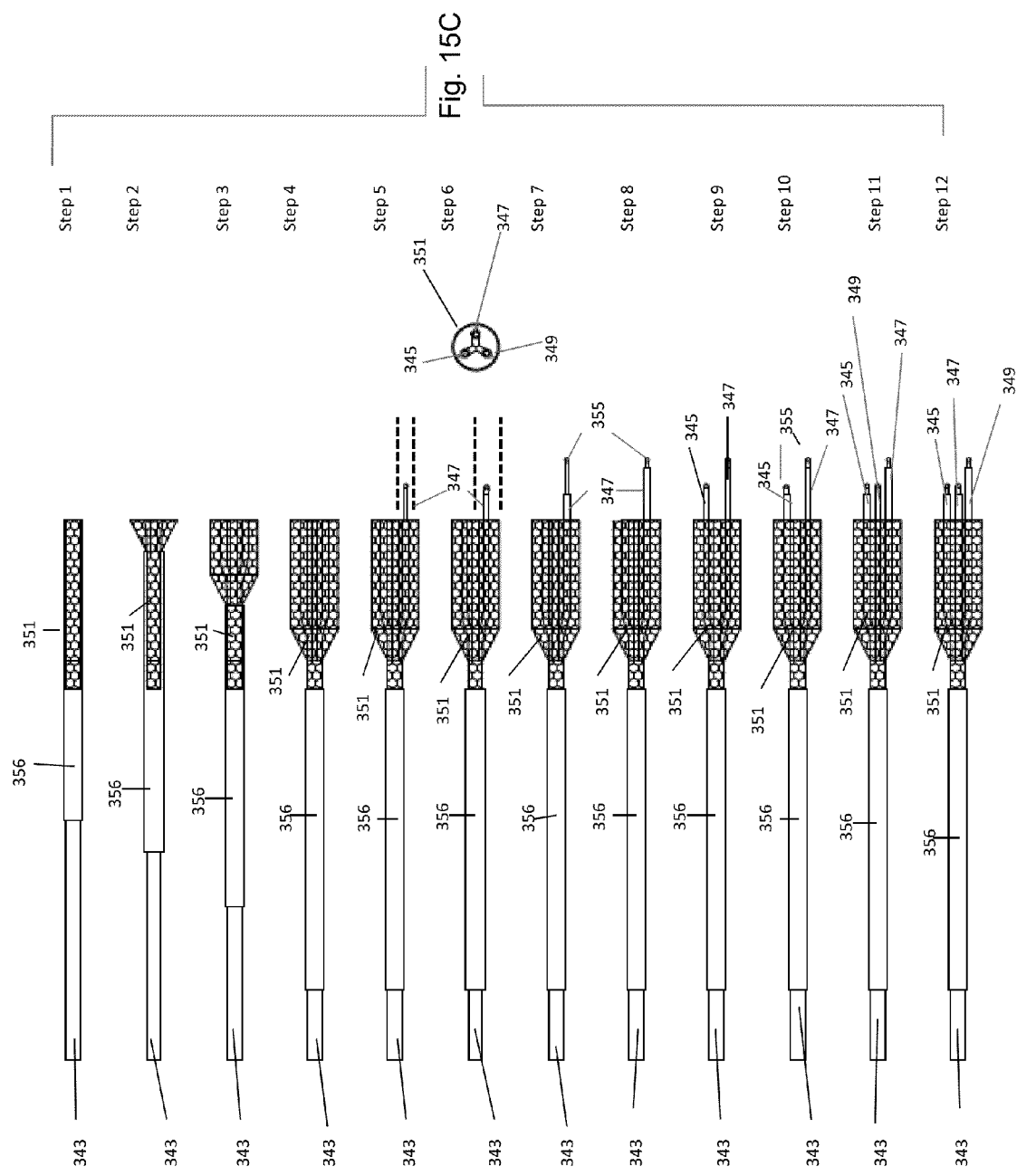

SECTION A-A

CATHETER APPARATUS WITH TELESCOPING LUMEN CATHETERS AND ITS USE IN METHODS FOR TREATING VASCULATURES

CROSS-REFERENCE TO RELATED APPLICATIONS

This application is a continuation-in-part application of U.S. application Ser. No. 13/166,623, filed Jun. 22, 2011, which is a divisional application of U.S. patent application Ser. No. 12/147,130, filed Jun. 26, 2008 (now U.S. Pat. No. 7,988,646 (issued Aug. 2, 2011)), which claims priority to U.S. Provisional Application No. 60/929,395, filed Jun. 26, 2007, U.S. Provisional Application No. 60/960,900, filed Oct. 19, 2007, U.S. Provisional Application No. 60/996,057, filed Oct. 26, 2007, and U.S. Provisional Application No. 61/064,715, filed Mar. 21, 2008, the contents of which are incorporated herein in their entireties. This application also claims priority to U.S. provisional application No. 61/716,856, filed Oct. 22, 2012, the contents of which are incorporated by reference in its entirety.

FIELD OF THE INVENTION

The invention relates generally to apparatus and methods for treating vasculatures, and, more particularly, to methods and apparatus for passing one or more guidewires through a chronic total occlusion of a vasculature via the use of a catheter apparatus configured to contain one or more telescoping lumen catheters.

BACKGROUND OF THE INVENTION

A chronic total occlusion in a coronary artery, peripheral artery, vein, dialysis fistula, or other types of vasculature represents a challenge for percutaneous treatment. Percutaneous treatments are generally preferred revascularization options as compared to bypass surgery. Continuing improvements in equipment specifically developed for chronic total occlusions have allowed success rates to improve. Although the success rates for these types of procedures have improved, the procedures for percutaneous treatments still suffer from several drawbacks. Patients without a successful percutaneous treatment may need to undergo bypass surgery or experience continuing symptoms from the occlusions.

A major obstacle within a chronic total occlusion may often be encountered while attempting to advance a guidewire across the chronic total occlusion in a vasculature. A maximum resistance may be met at the most proximal point of the lesion, i.e. the firm, fibrous cap. While being advanced, a guidewire may tend to deflect away from the fibrous cap towards the adventitial layer, often entering a false lumen. This off-axis displacement of the guidewire often may result in a procedural failure.

Successful passage of the guidewire may also be obstructed by randomly located calcified regions of atherosclerotic plaque within the mass of the lesion. Microchannels within the obstruction may be desirable targets for the tip of the guidewire. However, these soft spots within the lesion are difficult to identify angiographically and are dispersed randomly within the matrix of the lesion.

Coronary arteries and other vasculatures tend to be non-linear conduits, often coursing over the surface of the epicardium and other tissues. The success of current technology is limited by this type of geometry. In current systems, a guidewire or currently available catheter is advanced down a vasculature to the level of the obstruction. At the point of the obstruction, the guidewire advancement may tend to proceed along the outer, greater curvature of the vasculature. Even a guidewire centered within the vasculature at the proximal edge of the chronic total occlusion may tend to proceed toward the outer, greater curvature of a vasculature.

As a result, only a minor portion of the surface area of the obstruction may be encountered with sufficient force to allow passage of the guidewire. On many occasions, the angle of encounter and/or the force applied to the fibrous cap may not be sufficient for crossing the fibrous cap with the guidewire. If the tip of the guidewire is curved prior to placement through the support catheter, direct longitudinal force may be compromised as the wire is advanced off axis. If a rapid exchange catheter system is used as catheter support, the guidewire may buckle within the guide-catheter resulting in suboptimal longitudinal guidewire force.

At times, a single lumen angioplasty balloon may be inflated just proximal to the chronic total occlusion in an attempt to center the guidewire in the vessel lumen and provide additional support for the guidewire. Atherosclerotic lesions tend to be asymmetric with an eccentric true lumen. Therefore, attempts to limit the guidewire to the central axis of the vessel lumen may result in lower rates of procedural success.

Generally, needs exist for improved apparatus and methods for treating vasculatures. More specifically, needs exist for improved apparatus and methods for efficiently and effectively passing a guidewire through a chronic total occlusion in a vasculature.

SUMMARY OF THE INVENTION

Embodiments of the present invention solve many of the problems and/or overcome many of the drawbacks and disadvantages of the prior art by providing an apparatus and method for treating vasculatures.

In particular, embodiments of the invention may accomplish this with an apparatus for efficiently and effectively passing a guidewire through a chronic total occlusion in a vasculature. The apparatus may have a flexible shaft having a distal end, one or more guidewire lumens having a distal end and passing longitudinally through the shaft, and a positioning means for positioning distal ends of the one or more guidewires relative to an inner wall of an external lumen. The apparatus may have one or more lumen catheters (such as e.g. 3), which may be jointly or independently movable such that the distal end of the one or more lumen catheters telescopes beyond the distal end of the flexible shaft. The one or more lumen catheters may also be jointly or separately (i.e. independently) operable. An actuator may control the operation of such lumen catheters. The lumen catheters are configured for passage of a guidewire.

The positioning means may be an expansible scaffold initially in a non-expanded state. A retractable sheath may surround the expansible scaffold and the retractable sheath may be retracted for expanding the expansible scaffold.

The positioning means may also be one or more balloons where the one or more balloons are inflated through an inflation port running longitudinally in the shaft. The positioning means may also include guidewire lumens coupled to or otherwise disposed within the expansible scaffold. The positioning means may also include inflatable means surrounding distal ends of the guidewire lumens. The inflatable means may or may not be located within an expansible scaffold.

The positioning means may also be a rotatable core within the shaft. The positioning means may also include a deflectable tip on the catheter. The positioning means may also include a shape-memory material integrated with the guidewire lumens.

A method of operating a catheter apparatus may include providing a catheter apparatus including a flexible shaft, one or more guidewire lumens passing longitudinally through the shaft, one or more guidewires within the one or more guidewire lumens, and a positioning means, inserting a guide catheter into a vasculature with a chronic total occlusion, inserting the catheter apparatus into the guide catheter, activating the positioning means for positioning the one or more guidewires relative to the chronic total occlusion, and advancing the one or more guidewires through the one or more guidewire lumens and into contact with the chronic total occlusion.

The one or more guidewires may be passed through the chronic total occlusion. The catheter apparatus may be withdrawn from the vasculature while leaving the one or more guidewires in place. The one or more guidewires may be withdrawn from contact with the chronic total occlusion and the one or more guidewires may be advanced through the one or more guidewire lumens into contact with the chronic total occlusion repeatedly until a suitable site for passing the one or more guidewires through the chronic total occlusion is found. The positioning means may be activated before each advancing of the one or more guidewires through the one or more guidewire lumens into contact with the chronic total occlusion.

Another embodiment of the present invention may be a catheter apparatus including a multi-lumen main shaft; one or more guidewire lumens extending from a distal end of the multi-lumen shaft with lumens within the one or more guidewire lumens contiguous with at least one of the multi-lumens of the multi-lumen main shaft; an expansible support structure coupled to the distal end of the multi-lumen shaft; one or more loops corresponding to each of the one or more guidewire lumens, wherein the one or more loops corresponding to each of the one or more guidewire lumens are coupled to the expansible support structure, and wherein the one or more loops corresponding to each of the one or more guidewire lumens project inward from the plane of the expansible support structure; and wherein the one or more guidewire lumens are threaded through the corresponding one or more loops.

Another embodiment of the invention is a catheter apparatus including: a main catheter shaft; one or more lumen telescoping catheters, each lumen catheter configured for passing over one or more guidewire; each lumen catheter capable of telescoping in and out from a distal end of the main catheter shaft; and an expansible support structure coupled to the distal end of the main catheter shaft, the expansible support structure configured so that each telescoping lumen microcatheter can telescope in and out of the expansible support structure. The main catheter shaft may have one or more telescoping lumen catheter shafts. The one or more telescoping lumen catheters may pass through the one or more telescoping lumen catheter shafts. The telescoping lumen catheters may be coupled to the expansible support structure. The expansible support structure may be self-expanding and it may be a scaffold.

The expansible support structure may be capable of surrounding the one or more telescoping lumen catheters. When the expansible support structure (e.g. scaffold) surrounds the one or more lumen catheters, the expansible support structure has one or more inward facing loops each corresponding to one or more of the telescoping lumen catheters and wherein each of the one or more telescoping lumen catheters are threaded through the corresponding one or more loops. These one or more inward facing loops may be coupled to the expansible support structure by loop connections. The expansible support structure may include closed cells. These closed cells, for example, may be approximately hexagonal with expansible S-shaped connectors on two opposing sides of the hexagon. The expansible support structure may be made from a shape memory alloy such as e.g. nitinol.

The apparatus may also include a retractable sheath covering at least a portion of the expansible support structure of the main catheter shaft, wherein retracting the sheath from the distal portion of the shaft directly activates the expansible support structure. The retractable sheath may be advanced around the expansible support structure to compress the expansible support structure. In addition, the apparatus may include an actuator. Operation of the actuator may control movement of the one or more telescoping lumen catheters.

The one or more telescoping lumen catheters may be capable of separately telescoping in and out of the main catheter shaft. For example, one telescoping lumen catheter may be capable of separately telescoping in and out of the main catheter shaft. Alternatively, two or more telescoping lumen catheters may be capable of separately telescoping in and out of the main catheter shaft. In one embodiment, the one or more telescoping lumen catheters surround the main catheter shaft and the distal tip of each of the one or more telescoping lumen catheters is coupled to the support structure.

Another embodiment of the invention is a catheter apparatus including a shaft having a proximal and a distal end; one or more telescoping lumen catheters surrounding the shaft, each telescoping lumen catheter configured for passing over one or more guidewires; each telescoping lumen catheter capable of telescoping the distal end the main catheter shaft; an support structure coupled to the distal end of the shaft, wherein the distal end of each lumen catheter is coupled to the scaffold. The coupling may be on the interior of the support structure (e.g. scaffold). The support structure may be self-expansible. The expansible support structure may be capable of surrounding the one or more telescoping lumen catheters. When the support structure surrounds the lumen catheters, the structure has one or more inward facing loops corresponding to each corresponding to one or more the telescoping lumen catheters and wherein each of the one or more telescoping lumen catheters are threaded through the corresponding one or more loops. The one or more inward facing loops may be coupled to the expansible support structure by loop connections. The expansible support structure may include closed cells which are approximately hexagonal with expansible S-shaped connectors on two opposing sides of the hexagon. Apparatus may also include a retractable sheath covering at least a portion of the expansible support structure of the main catheter shaft, wherein retracting the sheath from the distal portion of the shaft directly activates the expansible support structure.

Another embodiment of the invention is a method for advancing a guidewire through an obstructed vasculature including: inserting the catheter apparatus having a main shaft and one or more telescoping lumen catheter is passing, each telescoping lumen catheter configured for passing over one or more guidewires into an obstructed vasculature; expanding an expansible support structure on the distal end of the main shaft; telescoping one or more telescoping lumen catheters in and out of main catheter shaft and through the expanded support structure; and advancing one or more guidewires through the one or more telescoping lumen catheters and into contact with an obstruction. The main catheter shaft may have one or more telescoping lumen catheter shafts through which one or more telescoping lumen catheters is passing. The one or more telescoping lumen catheters may telescope individually. The one or more telescoping lumen catheters may provide support to the one or more guidewires.

The support structure may be a scaffold. The support structure may also be made from a shape memory alloy such as e.g. nitinol. The support structure may also be made of a self-expanding. When the support structure is self-expanding, the step of expanding the expansible support structure includes withdrawing a sheath surrounding the support structure. The expansible support structure may surround the one or more telescoping lumen catheters and may have one or more inward facing loops corresponding to each corresponding to one or more the telescoping lumen catheters and wherein each of the one or more telescoping lumen catheters are threaded through the corresponding one or more loops.

The step of telescoping may include telescoping the telescoping lumen catheters out of the main catheter until resistance is felt. The method may also include sequentially advancing the one or more telescoping lumen catheters. The step of telescoping may further include measuring the distance a telescoping lumen catheter advances and the method may also further include advancing the one or more guidewire through the telescoping lumen catheter that advances the furthest.

Additional features, advantages, and embodiments of the invention are set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE INVENTION

The accompanying drawings, which are included to provide a further understanding of the invention and are incorporated in and constitute a part of this specification, illustrate preferred embodiments of the invention and together with the detailed description serve to explain the principles of the invention. In the drawings:

FIG. 1J is a side view of a shorter constraining sheath.

FIG. 1K is a side view of a longer constraining sheath.

FIG. 5A is a perspective view a catheter apparatus with a rotating inner core.

FIG. 5B is a cross section view of a midpoint of the catheter apparatus of FIG. 5A.

FIG. 6A is a perspective view a catheter apparatus with a deflecting tip and stabilizing balloon.

FIG. 6B is a cross section view of a midpoint of the catheter apparatus of FIG. 6A.

FIG. 8C illustrates the retraction of a retractable sheath from the catheter apparatus of FIG. 8A and FIG. 8B.

FIG. 8D illustrates the retraction of a retractable sheath as in FIG. 8C within a vasculature.

FIG. 9B illustrates the retraction of a retractable sheath from the catheter apparatus of FIG. 9A.

FIG. 10 illustrates the retraction of a retractable sheath from a catheter apparatus with shape-memory materials integrated with guidewire lumens.

FIG. 11 illustrates the retraction of a retractable sheath from a catheter apparatus and expansion of sponges surrounding guidewire lumens.

FIG. 12B is an unwrapped view of the loop embodiment of FIG. 12A.

FIG. 14A to E show a schematic view of a catheter having telescoping lumen catheters.

Figure 15A:
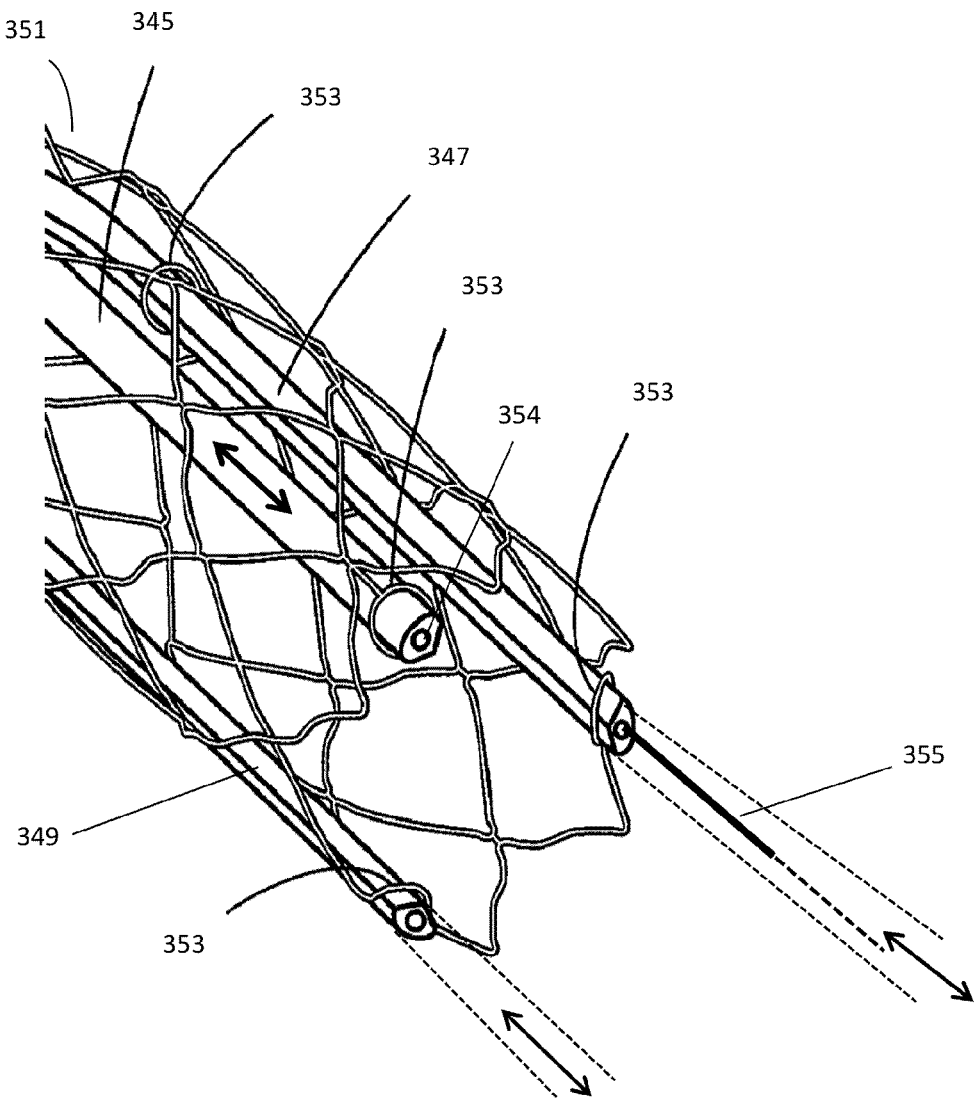
Figure 15B:
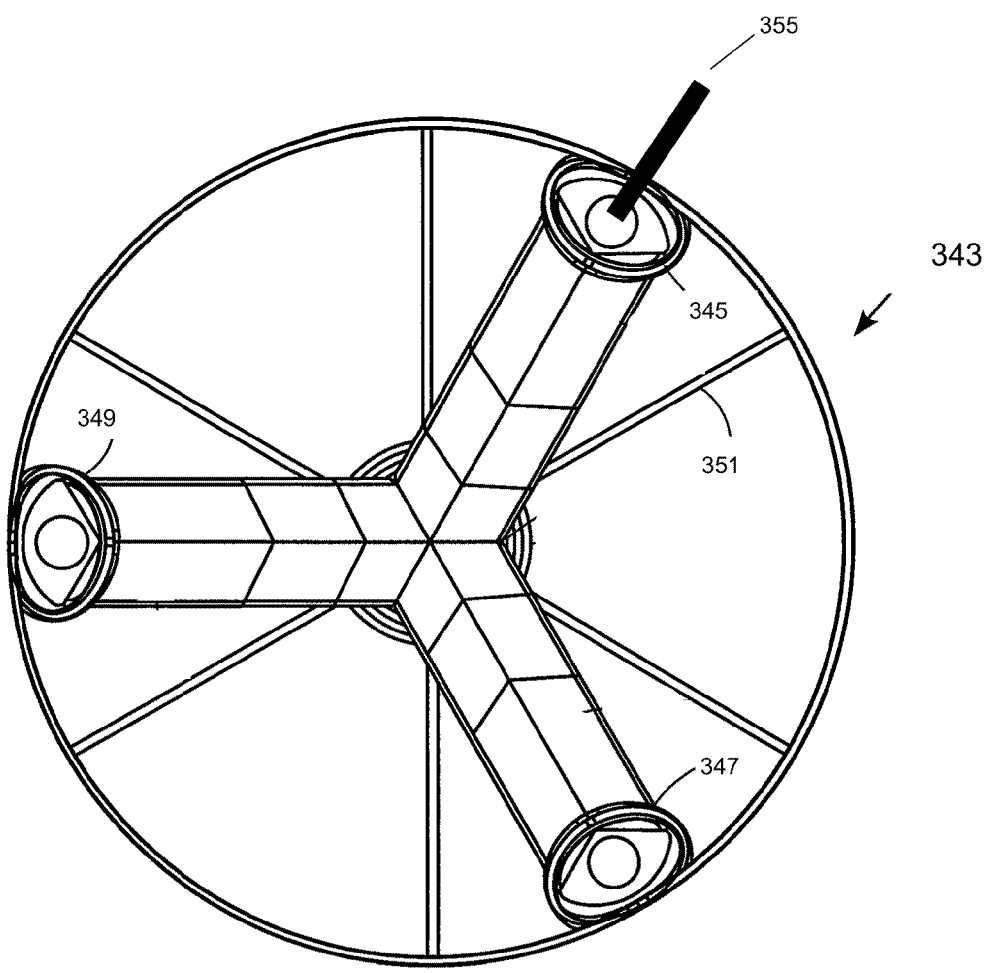

FIG. 15A to C show a distal end view of a catheter having telescoping lumen catheters.

Figure 16A:
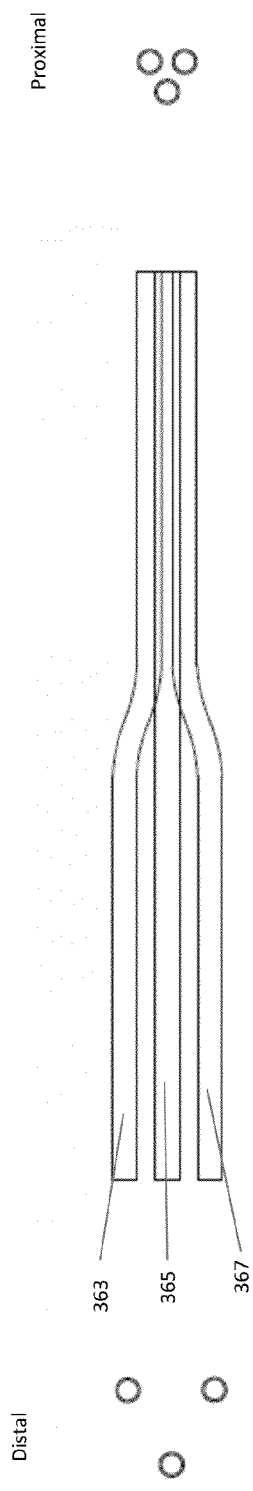
Figure 16B:
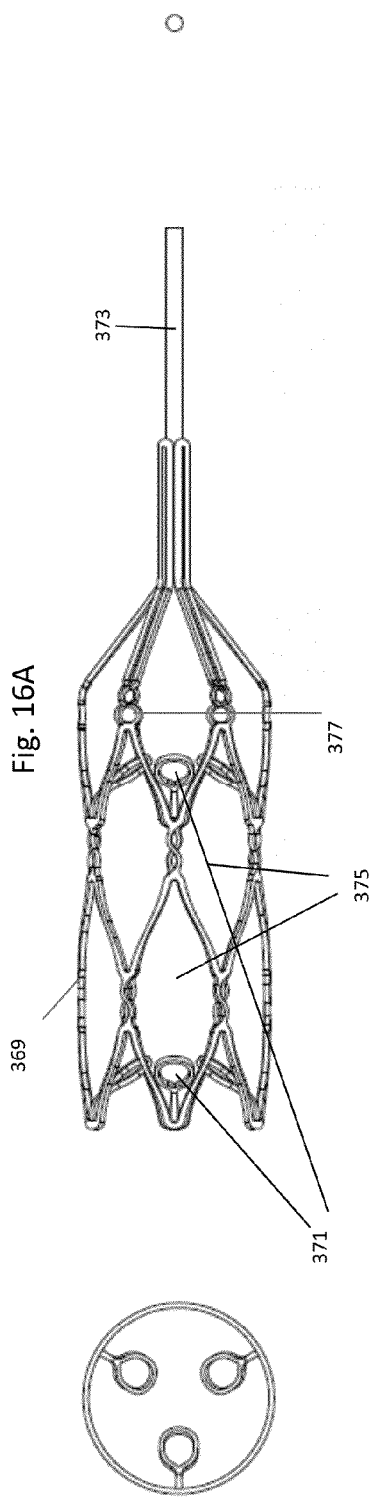
Figure 16C:
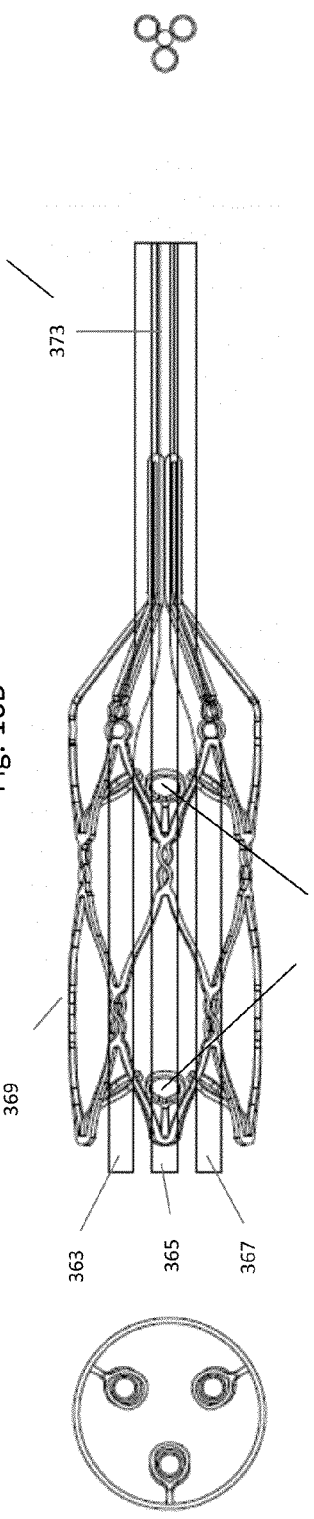

FIG. 16A to C show another embodiment of a catheter having telescoping lumen catheters.

Figure 17A:
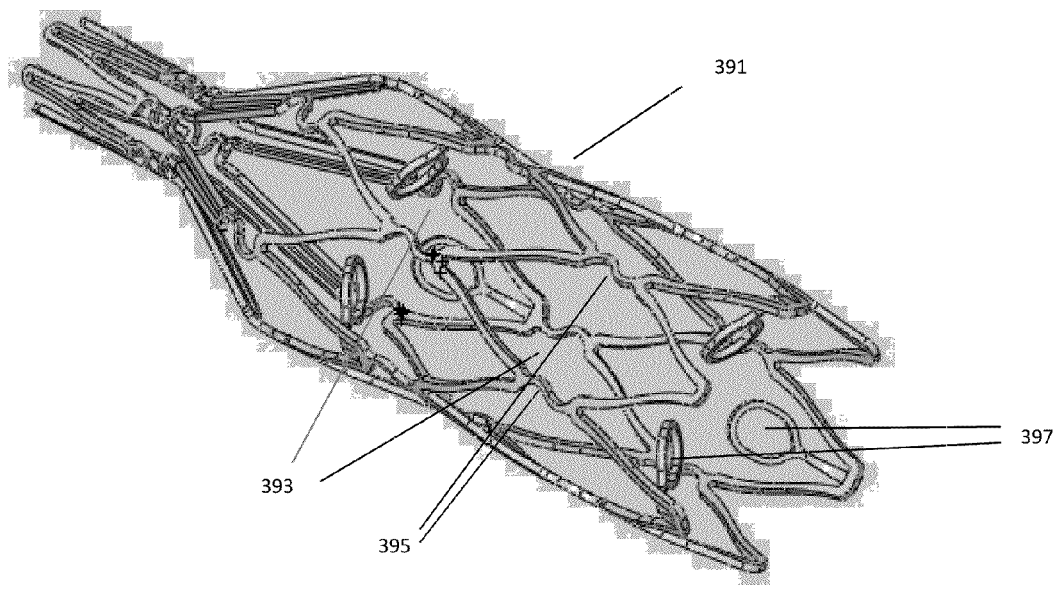

FIG. 17A is a perspective view of a loop embodiment in an expanded state.

Figure 17B:
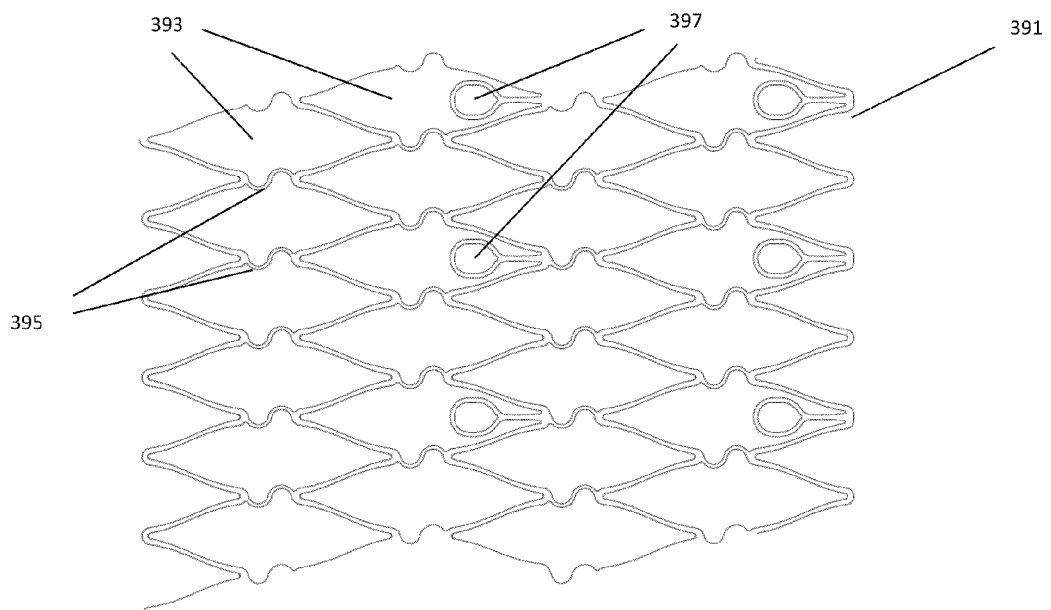

FIG. 17B is an unwrapped view of the loop embodiment of FIG. 17A.

Figures 18A, 18B:
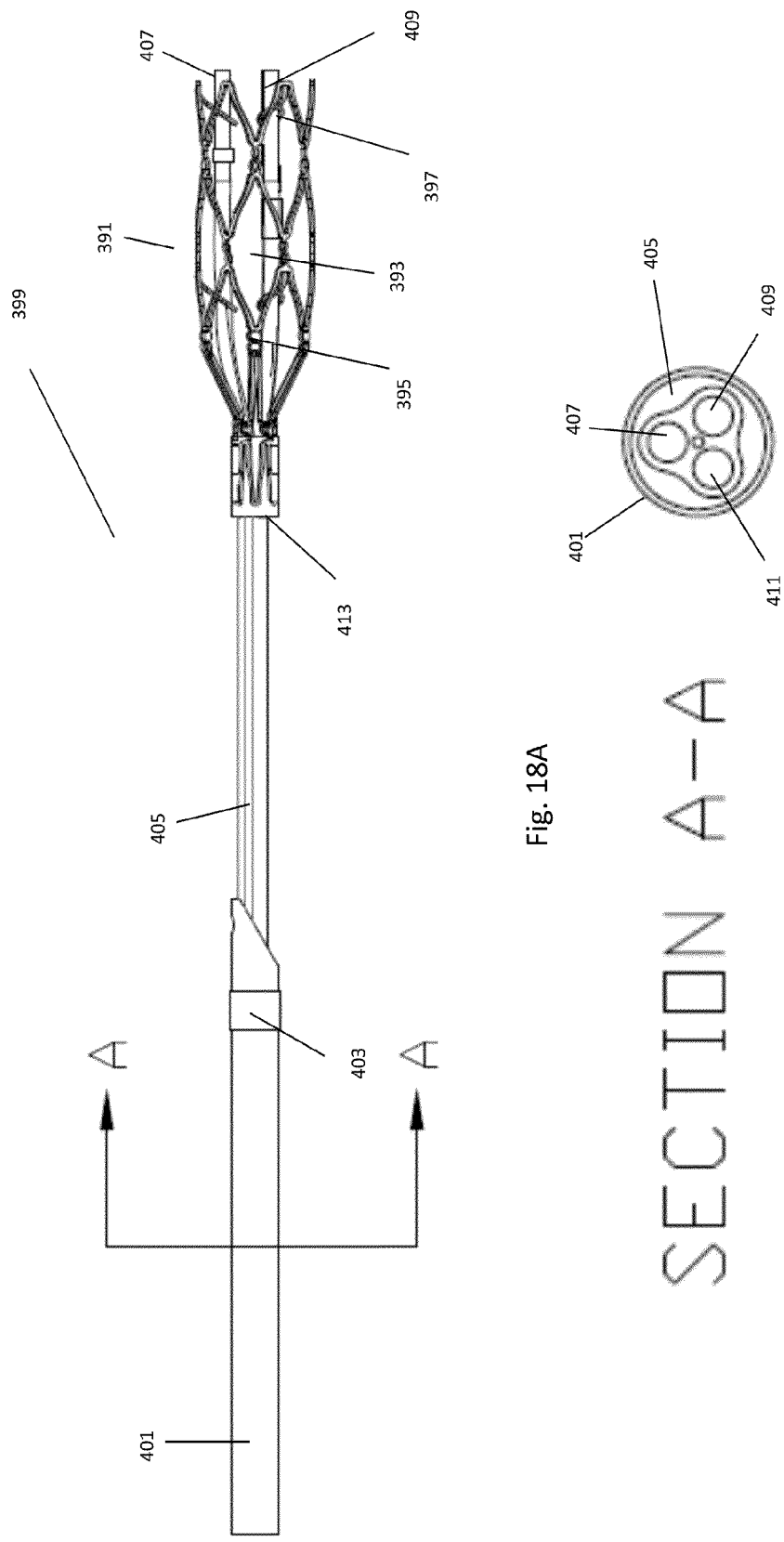
Figure 18C:
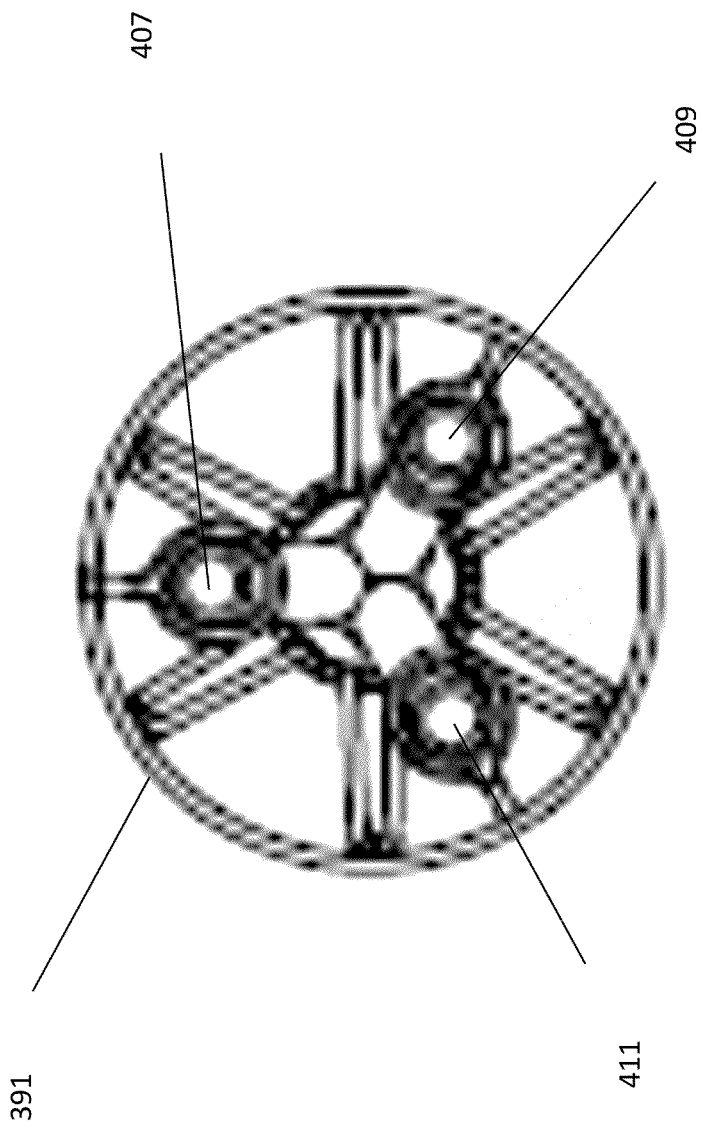

FIG. 18A to C show another embodiment of a catheter apparatus in accordance with the invention.

DETAILED DESCRIPTION OF THE PREFERRED EMBODIMENTS

Embodiments of the present invention may include apparatus and methods for advancing one or more guidewires through an obstructed vasculatures such as e.g. chronic total occlusions (CTOs) in vasculatures. The support and centering functionality has application beyond CTOs, even though the preferred embodiments described herein are directed to support and centering to facilitate a guidewire to cross through a CTO.

Embodiments of the present invention may incorporate several features to successfully pass one or more guidewires through an obstructed vasculature such as e.g. a chronic total occlusion. Features of the present invention may include multiple lumens constructed within a catheter shaft, expansion, or activation of a distal tip of a catheter apparatus for creating a scaffold effect, and/or decentralization of the guidewire lumens after activation or distal catheter repositioning for allowing multiple sections of a fibrous cap to be forcefully engaged by a guidewire. Features of the present invention may further include one or more lumen catheters that may be independently (separately) or jointly movable and, therefore, be advanceable beyond the distal end of the catheter shaft. For example, the multiple lumen catheters may be telescoping beyond the distal end of the catheter shaft. Embodiments of the present invention may optimize advancement of the one or more guidewires into multiple sections of a fibrous cap of a chronic total occlusion with reasonable force.

In embodiments of the present invention, one or more over-the-wire lumens may be constructed within a shaft of a catheter apparatus. Embodiments of the present invention may preferably use two or more lumens such as e.g. three lumens. The lumen may be configured to accommodate lumen catheters. The lumen catheters may be independently advanceable. The lumen catheters may be advanceable so that the lumen catheters may extend (e.g. telescope) beyond the shaft of the catheter apparatus. In addition, the lumen catheters may retract into the shaft of the catheter apparatus. Larger vasculatures, such as coronary arteries, may accommodate higher profile catheters and allow use of additional lumens. Each lumen may accommodate at least a 0.014" diameter guidewire. Other sized lumens and guidewires may be accommodated based upon the desired end use. Standard off-the-shelf or customized guidewires may be used. For example, in addition to traditional guidewires, embodiments of the present invention may be used with guidewires including, but not limited to, steerable, hydrophilic, Teflon-coated, heparin-coated, ball-tip, J-tip, spiral tip, angulated wire and others.

Embodiments of the present invention may be combined with other types of catheter devices. The positioning systems and methods of the present invention may be to deliver and/or direct other catheters towards a desired position. For example, a vibrating catheter or other specialized catheter may be directed towards a chronic total occlusion or other location in a vasculature. A microcatheter with a distal positioning device, including, for example, one or more balloons that may be inflated individually, sequentially or simultaneously, or other features, may be placed in proximity to a chronic total occlusion. A positioning system may steer the microcatheter away from a wall of a vessel, as it probes a cap of a chronic total occlusion. Microcatheters with angulation or other features may be placed in proximity to a chronic total occlusion where the angulation steers away from a wall of a vessel, probes a cap of a chronic total occlusion or otherwise changes directions. A catheter portion and/or sheath of embodiments of the present invention may be large enough to deliver and/or position specialized catheters to a desired location. Positioning devices may then be used to position the specialized catheters in a beneficial manner for a procedure.

In particular, embodiments of the present invention may deliver energy via the guidewires through radio frequencies and/or lasers. Furthermore, other types of energy may be delivered such as direct conductive heat energy, infrared or other types of energy that may be useful in particular applications. Various types of guidewires and/or delivering energy via guidewires may allow for various types of treatments. The external diameter of a catheter apparatus of the present invention may allow passage through a standard guide catheter. The outer surface of a catheter apparatus of the present invention may be coated with hydrophilic material to allow easier passage through the guide catheter. With alternate dimensions, the catheter apparatus of the present invention may be used in peripheral vessels. In this situation, a guide catheter may not be necessary to insert the device into the vasculature.

FIGS. 1A-1K show a self-expanding catheter apparatus 11. The external diameter of the self-expanding catheter apparatus 11 may pass through a sheath 19.

The sheath 19 may be a separate element surrounding the distal end of the catheter apparatus 11 to maintain the catheter apparatus 11 in an inactive state. The sheath 19 may have a rounded or tapered end for facilitating passage through a vasculature. Other end configurations are possible depending on particular uses.

Additional embodiments of the sheath may be shown in FIGS. 1J-1K. A sheath 68, 69 may be used to lower a profile of a self-expanding distal portion 13 of the catheter apparatus 11, which may preferably be a nitinol component, during insertion and removal of the catheter apparatus 11 from a vasculature. A sheath 68 may have a shorter configuration, as shown in FIG. 1J, covering at least a distal self-expanding component, preferably a nitinol element, on the catheter apparatus 11. The sheath 68, however, may preferably be long enough to correspond to the length of the treated vasculature, i.e., long enough to cover the portion of the catheter extending outside of a guide catheter and into the vasculature. This sheath configuration may function by insertion through a guide catheter and advancement into a treated vasculature. The sheath 68 may be attached 60 to a solid core guidewire and/or flexible device 67. The solid core guidewire and/or flexible device 67 may be long enough to traverse a guide catheter. The solid core guidewire and/or flexible device 67 may be a solid structure with no internal lumens and may preferably be made of plastic or similar materials. The solid core guidewire and/or flexible device 67 may be manipulated from outside the body, preferably by means of an expanded element 64 at a proximal end of the solid core guidewire and/or flexible device 67. The solid core element 67 may parallel the catheter apparatus 11 through a guide catheter. A distal portion 58 of the sheath 68 may be flared to fit a self-expanding portion 13 of the catheter apparatus device 11. The distal portion 58 may also have one or more radiopaque or other types of markers 54. The sheath 68 may have a stop point to allow withdrawal of the sheath 68 to a predetermined position, which may also facilitate resheathing of the catheter apparatus 11.

Alternatively, as shown in FIG. 1K, a sheath 69 may have a longer length, completely surrounding an intravascular portion of the catheter apparatus 11 during insertion and removal. The sheath 69 may be a flexible with a roughly cylindrical shape. The sheath 69 may preferably be made of plastic or other similar materials. This sheath configuration may have a larger profile element 62 at an extra-vascular, proximal end, allowing for easier handling and movement of the sheath 69. A distal portion 66 of the sheath 69 may be flared to fit a self-expanding portion 13 of the catheter apparatus device 11. The distal portion 66 may also have one or more radiopaque or other types of markers 56. The sheath 69 may have a stop point to allow withdrawal of the sheath 69 to a predetermined position, which may also facilitate resheathing of the catheter apparatus 11. The sheath 69 may be used in conjunction with a guide catheter or may function without a guide catheter in a non-coronary vasculature.

A body or shaft 23 of the catheter apparatus 11 may be made of a flexible plastic material or any other similar substance. A hydrophilic coating may or may not be added to the outer surfaces of the catheter apparatus 11. One or more hubs 21 corresponding to one or more guidewires 15 and one or more lumens 17 may be disposed at a proximate end 29 of the catheter apparatus 11.

The one or more hubs 21 may be marked, color-coded, numbered or may otherwise differentiate between one another. Identification of individual guidewire lumens may allow more effective use of embodiments of the present invention. With marking, users may improve their ability to identify which guidewire lumen may be preferably used during a procedure. For example, if a particular guidewire lumen is in a preferable location relative to other guidewire lumens an operator may desire a quick and reliable method of inserting a guidewire through that particular guidewire lumen. Marking may save time and effort by eliminating trial and error to determine a desired guidewire lumen. Alternatively, marking may be useful for applications other than treatment of occluded vasculatures, such as steering guidewires through vasculatures via various lumens. For example, marking can allow embodiments of the present invention to be used in other areas and/or conditions of a vasculature, such as traversing the tortuous coronary arteries. Distal and proximal ends of the guidewire lumens may be similarly marked to identify the guidewire lumens. Distal ends or structures on distal ends of the guidewire lumens may be marked such that the user may identify a preferred guidewire lumen while the catheter apparatus is within a patient. Marking with radiopaque or other types of markers may include temporary structures within the guidewire lumens. For example, markers may be present on stylets within the guidewire lumens. The stylets may be removed if desired to reduce mass or otherwise improve efficiency of a procedure.

The one or more hubs 21 may allow introduction of stylets or other structures that run through the catheter apparatus to render it stiff or to remove debris from its lumen. The one or more hubs 21 may also allow passage of one or more guidewires 15.

Figure 1A:
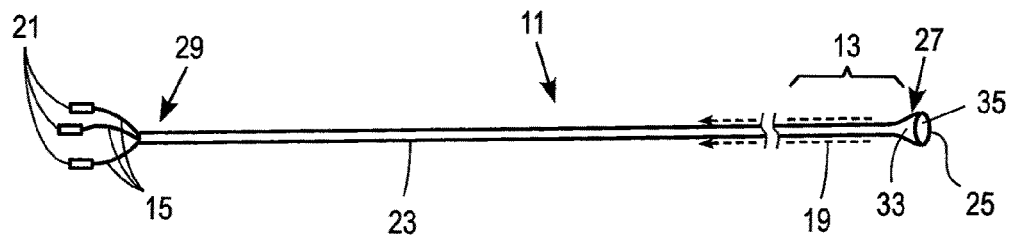
FIG. 1A is a perspective view of a self-expanding catheter apparatus.
Figure 1B:
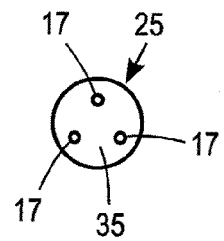
FIG. 1B is a distal end view of the catheter apparatus of FIG. 1A.
Figure 1C:
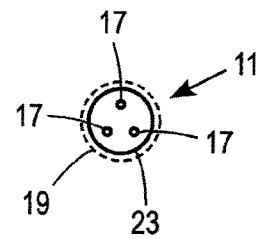
FIG. 1C is a cross section view of a midpoint of the catheter apparatus of FIG. 1A.

Generally, a distal portion 13 of the catheter apparatus 11 may function as a scaffold-type structure. The distal portion 13 of the catheter apparatus 11 may stabilize the catheter apparatus 11 within a vasculature lumen as one or more guidewires 15 are advanced into a chronic total occlusion. One or more guidewires 15 may be threaded through one or more lumens 17 within the catheter apparatus 11. The distal portion 13 of the catheter apparatus 11 is preferably self-expanding. FIG. 1B shows the distal end 25 of the catheter apparatus 11 in an expanded state. FIG. 1C shows a cross section of the catheter apparatus 11 with a retractable sheath 19 surrounding the body 23. The retractable sheath 19 may be retracted by moving the retractable sheath towards the proximate end 29 of the catheter apparatus 11. The distal portion 13 of the catheter apparatus 11 may include an activated scaffold structure 27 to stabilize the catheter apparatus 11. The activated scaffold structure 27 may expand to match a diameter of the vasculature lumen upon retraction of the retractable sheath 19.

Nitinol and/or stainless steel may be incorporated into the scaffold structure 27. Nitinol is an illustrative example of a shape memory alloy. Other shape memory alloys or other similar substances may be used. Generally, after a sample of a shape memory alloy has been deformed from its original crystallographic configuration, the shape memory alloy regains its original geometry by itself. This property of shape memory alloys may allow for expansion of the scaffold structure 27 after retraction of the retractable sheath 19. The nitinol and/or stainless steel scaffold structure 27 may create a stent-like mesh. The scaffold structure 27 may form the surface of the distal portion 13 of the catheter apparatus 11.

Figure 1D:
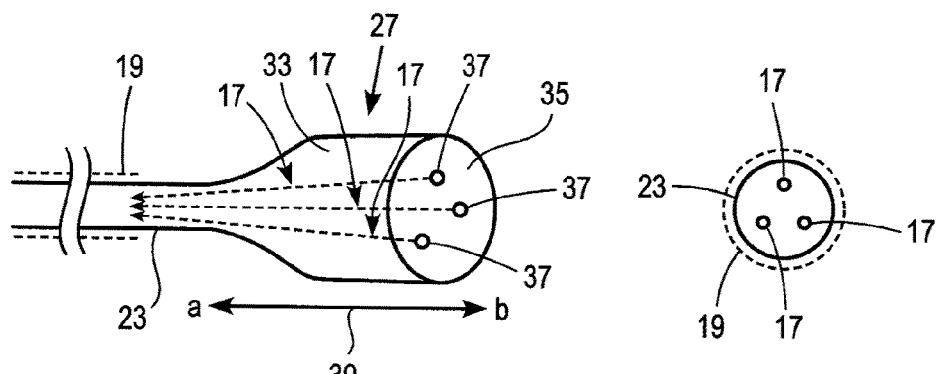
FIG. 1D is a perspective view of the self-expanding end of the catheter apparatus of FIG. 1A in an expanded state with a stop point.
Figure 1E:
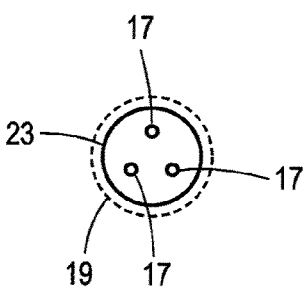
FIG. 1E is a cross section view of a midpoint of the catheter apparatus of FIG. 1D.
Figure 1F:
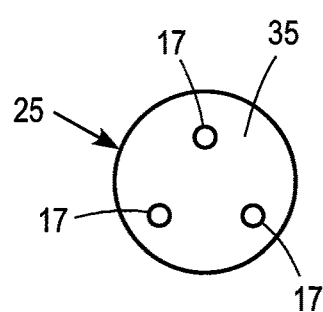
FIG. 1F is distal end view of the catheter apparatus of FIG. 1D.
Figure 1G:
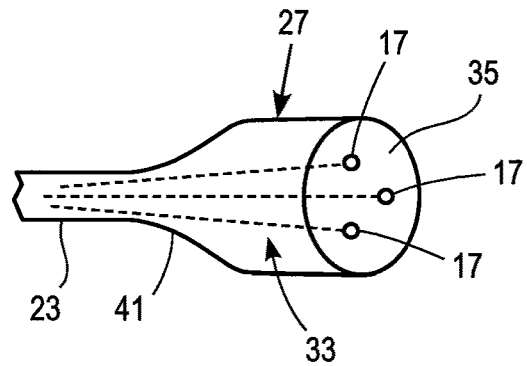
FIG. 1G is a perspective view of the self-expanding end of the catheter apparatus of FIG. 1A in an expanded state with a truncated conical portion.
Figure 1H:
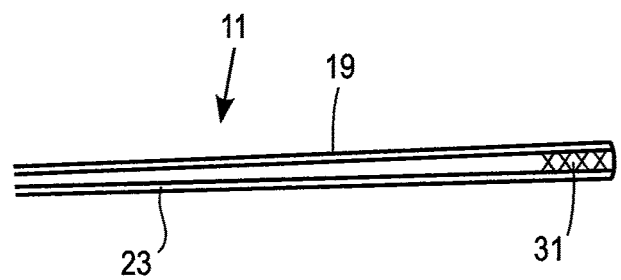
FIG. 1H is a side view of the catheter apparatus of FIG. 1A in a sheathed state.

FIG. 1H shows an inactive scaffold structure 31. The inactive scaffold structure 31 may be advanced over a guidewire into a chronic total occlusion with a retractable sheath 19 in place to constrain the self-expanding but inactive scaffold structure 31. The retractable sheath 19 may cover the inactive scaffold structure 31. When the inactive scaffold structure 31 is properly positioned, the retractable sheath 19 may be retracted by an appropriate retraction means. As the retractable sheath 19 is retracted, the inactive scaffold structure 31 of the catheter apparatus 11 may become active and may flare out. During a flare out process, the inactive scaffold structure 31 may self-expand to assume a larger diameter to roughly approximate the diameter of the vasculature in the location of the distal portion 13 of the catheter apparatus 11.

The retraction of the retractable sheath 19 may be a continuous or step-wise process. For example, the retractable sheath 19 may be retracted in one operation by a user until the scaffold structure 31 is fully exposed. Alternatively, the retractable sheath 19 may be retracted in increments less than that required for full expansion of the scaffold structure 31. Stop points during refraction of the retractable sheath 19 may allow for predetermined quantities of expansion of the scaffold structure 31. For example, if a procedure required less than full expansion of the scaffold structure 31, a stop point short of full retraction of the retractable sheath 19 may be chosen.

The conversion and expansion of the inactive scaffold structure 31 into an active scaffold structure 27 may create a relatively stable platform from which to advance the one or more guidewires 15 into multiple sections of the chronic total occlusion. The activated catheter apparatus 11 with the retractable sheath 19 retracted may have an activated scaffold structure shaped as a truncated cone or other suitable shape. A surface 33 of the expanded distal end 13 of the catheter apparatus 11 may consist of a "skin" of the scaffold structure 27. An end cap 35 may or may not cover the distal end 35 of the catheter apparatus 11. The end cap 35 may preferably be made of an impervious expandable polymer, but other similar substances may be used.

FIG. 1D shows an activated scaffold structure 27 that may be filled with an expandable polymer or similar material. The expandable polymer or similar material may fill the scaffold structure 27 to form a truncated, conical or other appropriate shape for securing the catheter apparatus 11 within the vasculature lumen. The expandable polymer may support distal portions of one or more guidewire lumens 17. Upon expansion of the expandable polymer, the embedded lumen ends 37 may flare out correspondingly with the end cap 35. FIG. 1E shows a cross section of the catheter apparatus 11 with the retractable sheath 19 surrounding the shaft 23. FIG. 1F shows an end view of the expanded end cap 35 with embedded guidewire lumens 17.

A skin 33 may surround the expandable polymer or similar material. The skin 33 may be a temporary metal "stent." The metal stent may be a mesh type structure. The metal stent may become a truncated conical shape after expansion or any other suitable shapes.

The a-b dimension 39 indicated in FIG. 1D may shorten when the retractable sheath 19 is removed from scaffold structure 27. The degree of shortening of the a-b dimension 39 may vary depending on the degree of expansion, the materials used, etc.

The retractable sheath 19 may be refracted to a stop point. The stop point may prevent over-retraction of the retractable sheath 19. A retractable sheath 19 at the stop point may facilitate re-sheathing of the scaffold structure 27.

FIG. 1G shows multiple guidewire lumens 17 that may be suspended within a scaffold structure 27 without using an expansible polymer or similar filler. A skin 33 may be made of nitinol, stainless steel, or another expansible substance. The one or more guidewire lumens 17 may extend to the distal end 25 of the scaffold structure 27. The scaffold structure 27 may begin roughly at a transition point 41. The one or more guidewire lumens 17 may or may not be embedded in an end cap 35. The end cap may an impervious plastic material.

Figure 1I:
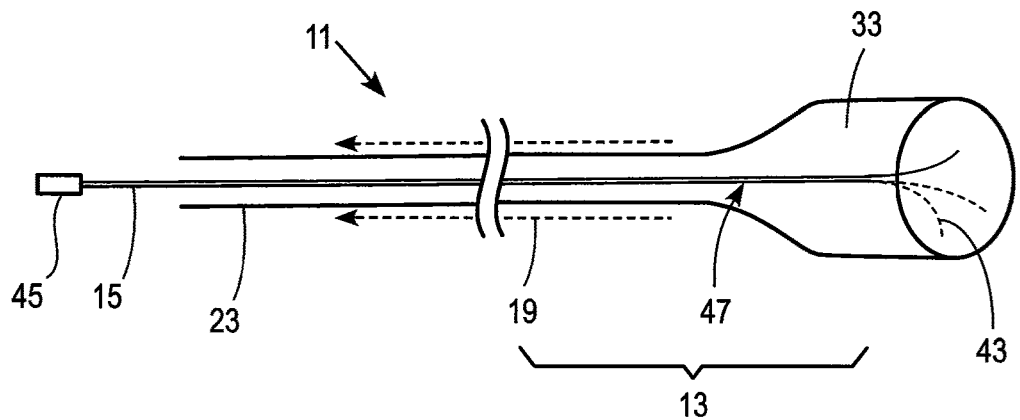
FIG. 1I is a perspective view of the catheter apparatus of FIG. 1A with a deflectable tip.

FIG. 1I shows a catheter apparatus with an expandable skin 33 and a deflectable tip 43. The deflectable tip 43 may be rotatable or otherwise moveable. The deflectable tip 43 may be rotatable with a rotator 45 or other similar device at the proximate end 29 of the catheter apparatus 11. The embodiment depicted in FIG. 1I preferably does not include and end cap 35. The lack of an end cap 35 may allow for freedom of movement of the deflectable tip 43. The distal portion 13 of the catheter apparatus 11 may flare after the retractable sheath 19 is retracted. A single, centrally located deflectable lumen 47 may allow a guidewire 15 to be advanced in numerous planes. The deflectable tip 43 may allow for controlled probing of the fibrous cap of a chronic total occlusion.

Other embodiments of the present invention may include one or more balloons at or near a distal end of a catheter apparatus. The one or more balloons may be circumferential. Alternatively, the one or more balloons may be offset and placed longitudinally. Other positions and arrangements are possible depending on particular situations.

Figure 2A:
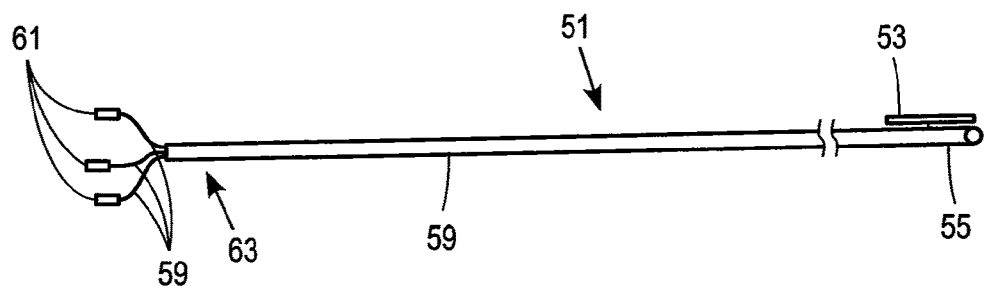
FIG. 2A is a perspective view of a catheter apparatus with a single balloon.

FIG. 2A shows an embodiment of the present invention with a balloon 53 that may be placed longitudinally near a distal tip 55 of a catheter apparatus 51. The balloon 53 may parallel the long axis of a shaft 59 of the catheter apparatus 51. Inflation of the balloon 53 may deflect the position of one or more guidewire lumens 57 relative to the fibrous cap of a chronic total occlusion. The balloon 53 may be inflated to a diameter that may buttress the catheter apparatus 51 against a wall of the vasculature lumen. The balloon 53 may then be deflated, the catheter apparatus 51 rotated, and the balloon 53 reinflated.

Figure 2B:
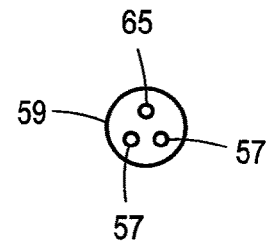
FIG. 2B is a cross section view of a midpoint of the catheter apparatus of FIG. 2A.

FIG. 2B shows a cross section of the catheter apparatus 51. The balloon 53 may be inflated and deflated through an inflation port 65. The inflation port 65 may pass through the shaft 59 to connect the balloon 53 to a proximate end 63 of the catheter apparatus 51. This method may result in one or more guidewires 59 probing various sections of the fibrous cap. One or more hubs 61 at the proximate end 63 of the catheter apparatus 51 may allow passage of the one or more guidewires 59. Stylets or other similar structures may be inserted or reinserted into the catheter apparatus 51 to facilitate rotation.

Figure 3A:
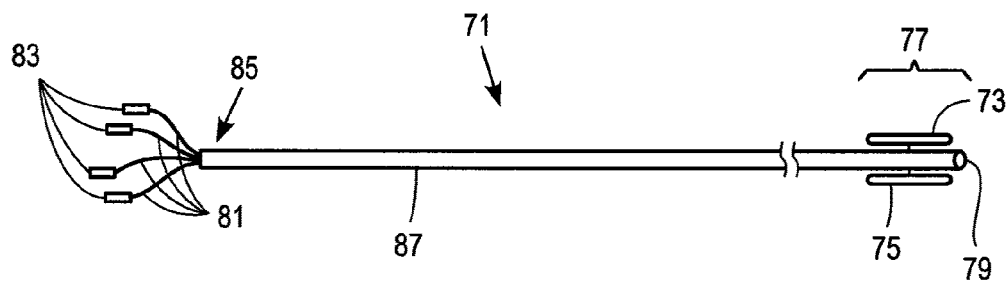
FIG. 3A is a perspective view of a catheter apparatus with double balloons.

FIG. 3A shows an embodiment of the present invention with a first longitudinal balloon 73 and a second longitudinal balloon 75 positioned near a distal end 77 of a catheter apparatus 71. More balloons may be used for additional or different control of the catheter apparatus. The multiple balloons 73, 75 may be inflated individually, simultaneously, alternatively or sequentially depending on the particular circumstances. The pattern of inflation and/or deflation of the multiple balloons 73, 75 may allow redirection of a distal catheter tip 79 relative to a fibrous cap of a chronic total occlusion. Repositioning of the distal catheter tip 79 may permit more complete interrogation of the fibrous cap with one or more guidewires 81. One or more hubs 83 at the proximate end 85 of the catheter apparatus 71 may allow passage of the one or more guidewires 81 through a shaft 87.

Figure 3B:
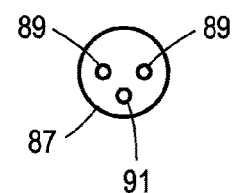
FIG. 3B is a cross section view of a midpoint of the catheter apparatus of FIG. 3A.

FIG. 3B shows a cross section of the catheter apparatus 71. One or more guidewire lumens 89 may pass through the catheter apparatus 71. Embodiments of the present invention may be constructed with multiple inflation ports (not shown) or with one inflation port 91 servicing the multiple balloons 73, 75. If the latter option is utilized, the balloon materials may be constructed to allow selective, and/or sequential inflations at increasing balloon pressures. The balloons 73, 75 may be positioned at various angles relative to one another around the circumference of the shaft 87.

Figure 4A:
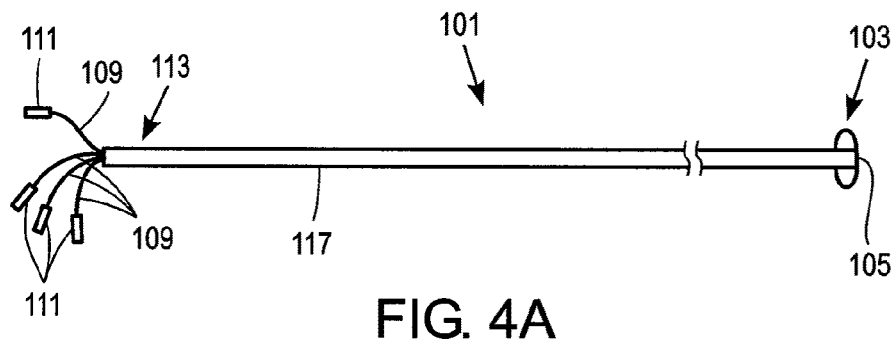
FIG. 4A is a perspective view of a catheter apparatus with a balloon.
Figure 4B:
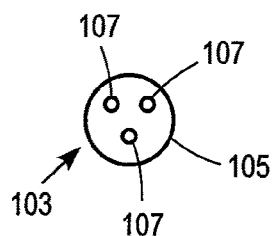
FIG. 4B is a distal end view of the catheter apparatus of FIG. 4A.
Figure 4C:
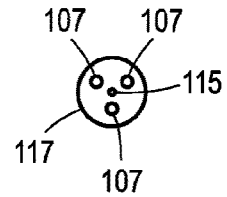
FIG. 4C is a cross section view of a midpoint of the catheter apparatus of FIG. 4A.

FIG. 4A shows an embodiment of the present invention with a balloon 103 with a distal surface 105 in a catheter apparatus 101. The balloon 103 may be flat, cylindrical, or any other suitable configuration. Additionally, the balloon 103 may be sectioned. One or more guidewire lumens 107 may be extruded through the balloon material. The balloon 103 may be inflated to match the inner diameter of the vasculature lumen. FIG. 4B shows an end view of the catheter apparatus 101. As the balloon 103 expands, the one or more guidewire lumens 107 extruded through the balloon 103 may diverge relative to one another in reaction to expansion of the balloon 103. The divergence may allow one or more guidewires 109 to probe various sections of the fibrous cap of the chronic total occlusion. One or more hubs 111 at the proximate end 113 of the catheter apparatus 101 may allow passage of the one or more guidewires 109. FIG. 4C shows a cross section of the catheter apparatus 101. A balloon inflation port 115 may pass through a shaft 117 with the one or more lumens 107 to inflate and/or deflate the balloon 103.

FIG. 5A shows a catheter apparatus 121 with an inner core 123 within an outer core 125. The inner core 123 may contain one or more lumens 127. Embodiments of the present invention may preferably include two or more lumens 127. FIG. 5B illustrates an embodiment with two lumens placed at positions of 3 o'clock and 9 o'clock within the inner core 123. Other quantities of lumens 127 and positions are contemplated for various applications and situations. The inner core 123 may be rotated within the outer shell 125 of the catheter apparatus 121 by turning or otherwise manipulating a rotator 129 at a proximate end 131 of the catheter apparatus 121. The rotator 129 may be coupled 133 or otherwise connected to the inner core 123. One or more guidewires 135 may be connected to one or more hubs 137 at the proximate end 131 of the catheter apparatus 121. The one or more guidewires may extend from a distal end 139 of the catheter apparatus 121.

A rotatable inner core 123 of catheter apparatus 121 may be used in conjunction with the various balloon configurations described above. For example, if constructed with a non-longitudinal stabilizing balloon, the shape of the distal tip balloon may be circumferential, i.e., doughnut-shaped.

FIG. 6A shows an embodiment of the present invention with a single stabilizing balloon 143 and a deflecting tip 145 on a catheter apparatus 141. The single stabilizing balloon 143 may be used in conjunction with a deflectable distal catheter tip 145 for eccentric placement of one or more guidewires 147. The one or more guidewires 147 may be passed through one or more hubs 149 at a proximate end 151 of the catheter apparatus 141. FIG. 6B shows a cross section of the catheter apparatus 141. One or more lumens 153 may pass through a shaft 155. An inflation port 157 may allow inflation and/or deflation of the stabilizing balloon 143. The deflecting tip 145 may be located at various angles depending on the particular situation.

Catheter apparatus shafts 23, 59, 87, 117, 12, and 155 may be constructed with either a circular, oval, or rectangular shape. Other shapes are possible depending on particular uses.

Figure 7A:
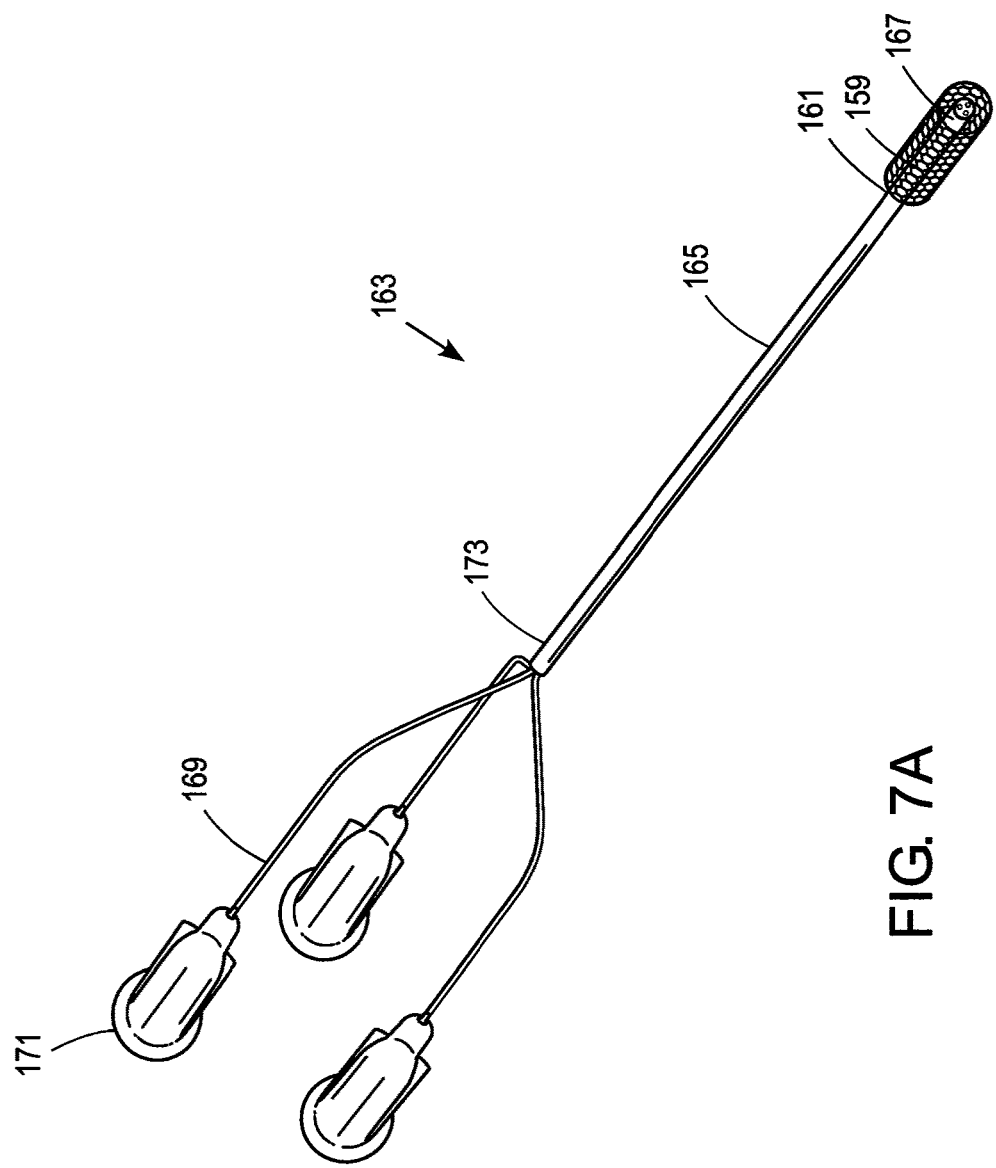
FIG. 7A is a perspective view of a catheter apparatus with an expansible mesh tip.

FIG. 7A shows an embodiment of the present invention with an expansible portion 159 at a distal tip 161 of a catheter apparatus 163. The expansible portion 159 may be a mesh or other similar configuration as described above. The expansible portion 159 may be expanded by retracting a retracting sheath 165 away from the distal tip 161 of the catheter apparatus 163. The expansible portion 159 may be expanded into contact with a wall of a vasculature.

Figure 7B:
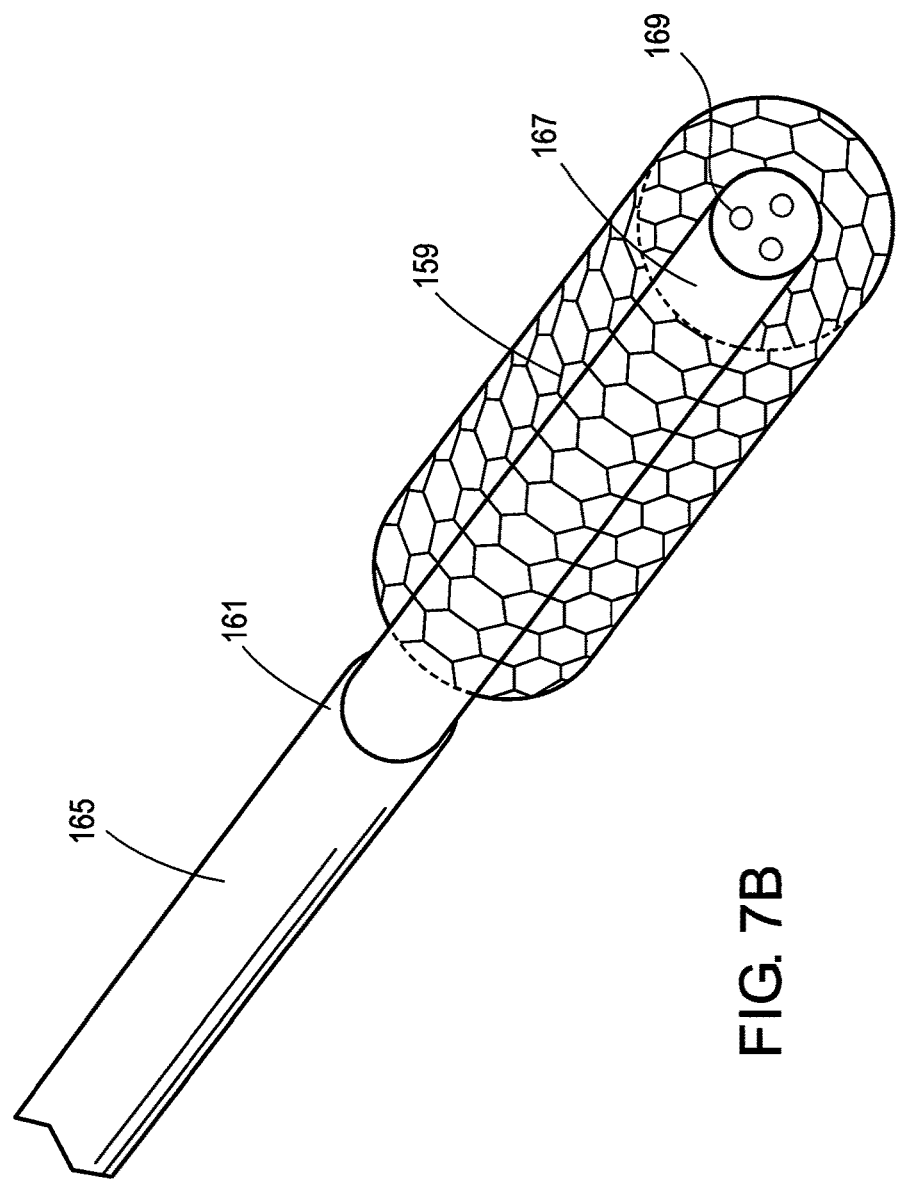
FIG. 7B is a detail of the catheter apparatus of FIG. 7A.

FIG. 7B shows a detail of the catheter apparatus 163. A central core 167 may contain one or more guidewire lumens 169. The central core 167 may or may not be expandable. The central core 167 may be rotatable to allow one or more guidewires 169 to probe various sections of a fibrous cap. One or more hubs 171 at the proximate end 173 of the catheter apparatus 163 may allow passage of the one or more guidewires 169.

Figure 8A:
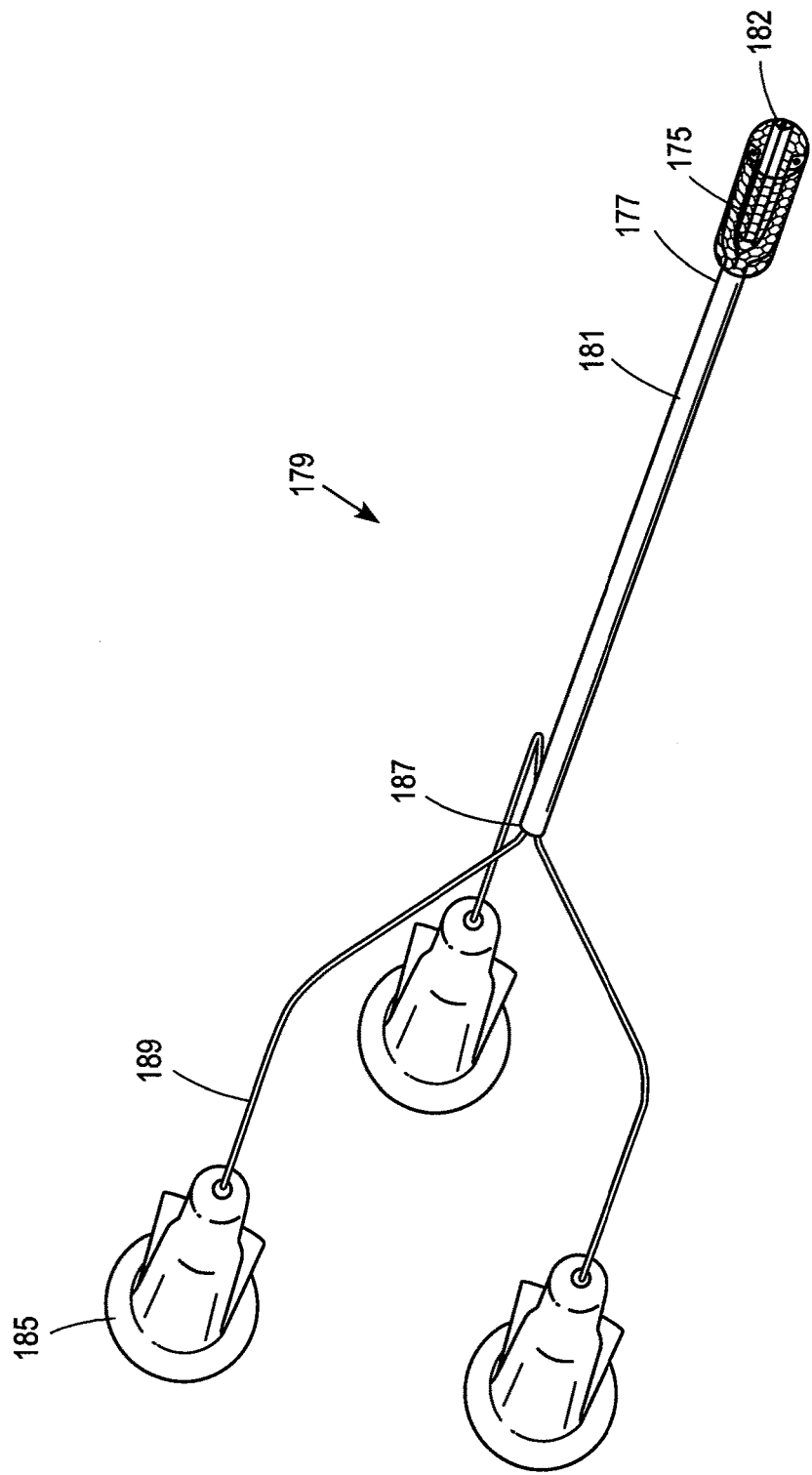
FIG. 8A is a perspective view of a catheter apparatus with guidewire lumens coupled to an expansible mesh tip.

FIG. 8A shows an embodiment of the present invention with an expansible portion 175 at a distal tip 177 of a catheter apparatus 179. The expansible portion 175 may be a mesh or other similar configuration as described above. The expansible portion 175 may be expanded by retracting a retracting sheath 181 away from the distal tip 177 of the catheter apparatus 179. The expansible portion 175 may be expanded into contact with a wall of a vasculature. One or more hubs 185 at the proximate end 187 of the catheter apparatus 179 may allow passage of the one or more guidewires 189.

Figure 8B:
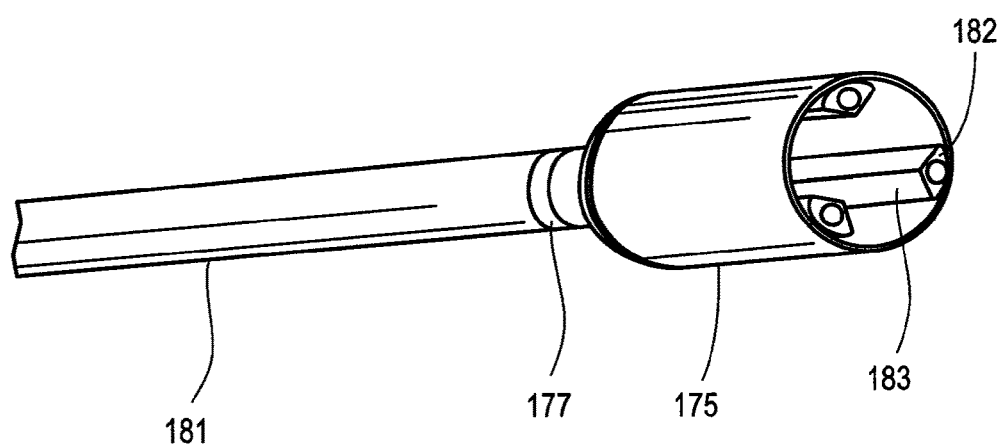
FIG. 8B is a detail of the catheter apparatus of FIG. 8A.

FIG. 8B shows a detail of the catheter apparatus 179. One or more guidewire lumens 183 may be formed of extruded plastic or similar materials. The figures generally illustrate three guidewire lumens 183, but other numbers and configurations may be desirable depending on particular uses. The one or more guidewire lumens 183 may have shape-memory alloys or other similar materials integrated into, surrounding or within the structure of the one or more guidewire lumens 183. Preferably, the one or more guidewire lumens 183 may self-expand upon retraction of the retraction sheath 181 such that ends 182 of the one or more guidewire lumens are spaced apart and approximately halfway between the center point and the inner surface of a vasculature. The one or more guidewire lumens 183 may be configured to expand into various predetermined positions and configurations depending on particular applications. For example, FIG. 8B shows a triangular configuration for the guidewire lumens 183. Other configurations are possible using three guidewire lumens 183. Furthermore, different numbers of guidewire lumens may be used in various configurations.

Alternatively, the one or more guidewire lumens 183 may be coupled to an inner surface of the expansible portion 175. The one or more guidewire lumens 183 may be adhered or integrally molded to the inner surface of the expansible portion 175.

Expansion of the expansible portion 175 may cause the one or more guidewire lumens 183 to separate via a self-expanding shape-memory material. Alternatively, the one or more guidewire lumens 183 may not be coupled to the expansible portion 175 but may instead be positioned within the internal volume of the expansible section 175 to allow probing of a fibrous cap. Additionally, a self-expanding polymer may fill the expansible portion 175. In an initial configuration the self-expanding polymer may be in a compressed state. As the expansible portion 175 is released from the retracting sheath 181, the self-expanding polymer may expand as well. The one or more guidewire lumens 183 may be embedded in the self-expanding polymer and may be moved into a desired position by the expansion of the self-expanding polymer. The self-expanding polymer may expand by absorbing moisture or blood from within the vasculature or through other expansion mechanisms. The self-expanding polymer may then be removed after a procedure.

FIG. 8C illustrates the operation of the catheter apparatus 179 of FIG. 8A and FIG. 8B. Similar operational procedures may be used for other embodiments described herein. Step 1 of FIG. 8C shows the catheter apparatus 179 in an initial state with a retractable outside sheath 181 moved as far as possible distally from a guidewire lumen tube 191. Steps 2-7 show incremental stages of retraction of the retractable outside sheath 181. As the retractable outside sheath 181 is retracted back over the guidewire lumen tube 191, the expansible portion 175 is incrementally exposed and allowed to expand. As the expansible portion 175 expands the one or more guidewire lumens 183 separate and are held in a desired position by the shape-memory alloy materials or by coupling to the expansible portion 175. Step 7 shows the expansible portion 175 in a fully deployed state. The end view of FIG. 8C shows the one or more guidewire lumens 183 in the fully deployed state. Step 8 shows a guidewire 189 inserted through a guidewire lumen 183. FIG. 8D illustrates the operation of the catheter apparatus 179 as shown in FIG. 8C within a vasculature 184 with an occlusion 186.

Figure 9A:
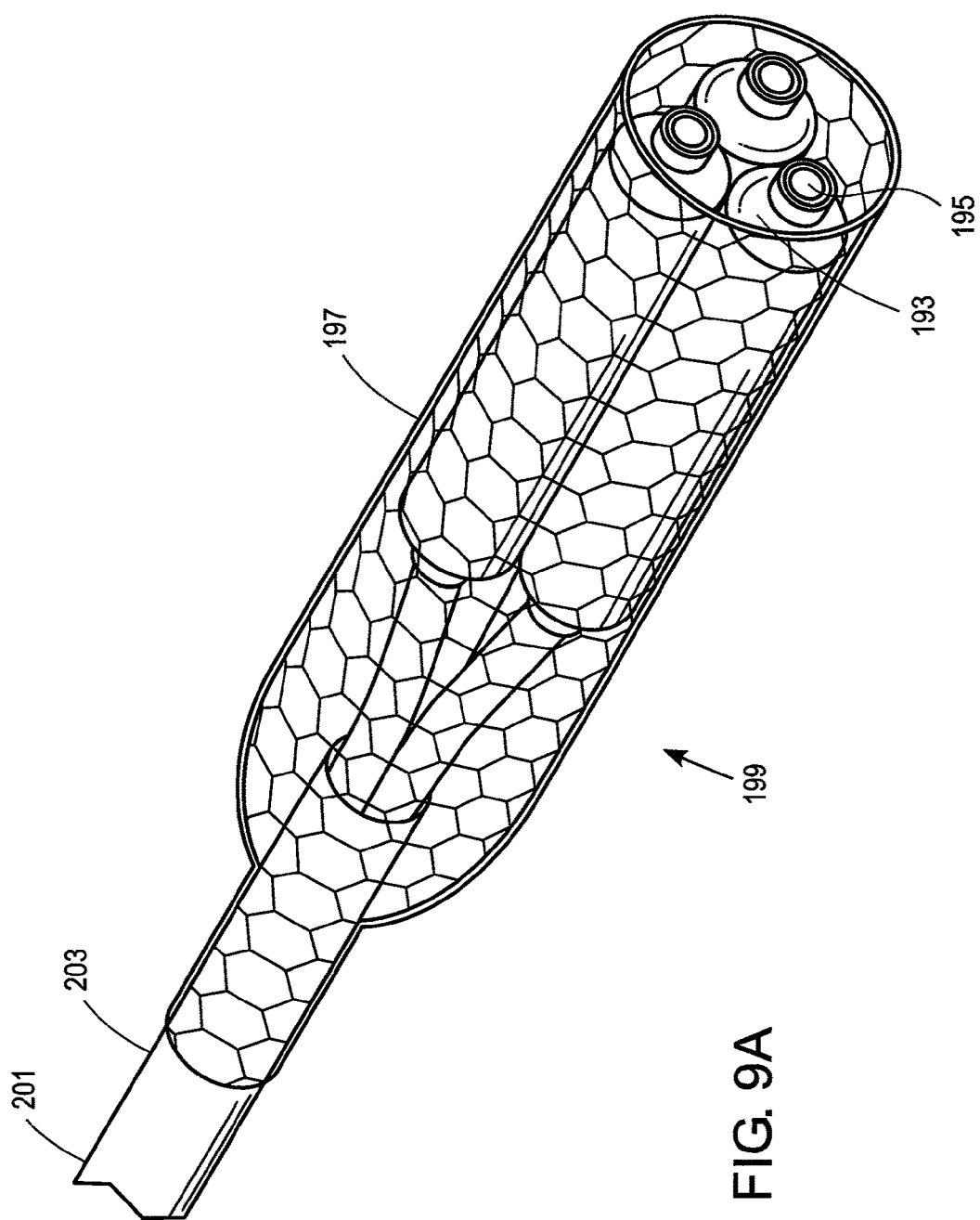
FIG. 9A is a perspective view of a catheter apparatus with expandable devices surrounding the lumen guidewires.

FIG. 9A shows an embodiment of the present invention with one or more inflatable devices 193 surrounding one or more guidewire lumens 195 within an expansible portion 197 of a catheter apparatus 199. The expansible portion 197 may be a mesh or other similar configuration as described above. The expansible portion 197 may be expanded by retracting a retracting sheath 201 away from a distal tip 203 of the catheter apparatus 199. The expansible portion 197 may be expanded into contact with a wall of a vasculature. The expansible portion 197 may be omitted as shown in FIG. 9B.

The inflatable devices 193 may initially be in a deflated condition during insertion and positioning of the catheter. The inflatable devices 193 preferably are balloons, but may be any other expansible type of device. The balloons may surround the outer surface of the one or more guidewire lumens 195. The balloons may be cylindrical or other shapes to position the one or more guidewire lumens 195 within the expansible portion 175. The inflatable devices 193 may include one balloon for each guidewire lumen 195 or one balloon may correspond to several guidewire lumens 195. For example, a single inflatable device 193 may be inflated to separate all of the guidewire lumens 195. Alternatively, two separate inflatable devices 193 may be used to separate three or more guidewire lumens. The inflatable devices 193 may be bifurcated or trifurcated depending on the number of guidewire lumens 195 and the particular application. The expansible sheath 197 may assist in containing multiple, separate inflatable devices 193, but may not be essential to the operation of the present invention.

One or more ports (not shown) may allow inflation or one or more of the inflatable devices 193 depending on the number of separate inflatable devices 193. For example, one port may be used to inflate one inflatable device 193. Alternatively, if two or more separate inflatable devices 193 are present, then two or more ports may be used to inflate and deflate the inflatable devices 193 serially or in parallel depending on a particular use or condition. Different numbers and combinations of inflatable devices and ports may be possible. Inflation of various combinations of inflatable devices 193 with various numbers and configurations of ports may allow for probing of a fibrous cap. If ends of the one or more guidewire lumens 195 or the inflatable devices 193 themselves are marked, a user may inflate specific inflatable devices 193 but not others to more accurately interrogate an occlusion. Each of the inflatable devices 193 may be inflated into contact with the expanded expansible portion 197 to secure the position of the one or more guidewire lumens 195. Guidewires (not shown) may then be passed through the one or more guidewire lumens 195. The inflatable devices 193 may be deflated prior to withdrawing the catheter apparatus 199.

As shown in FIG. 9B an embodiment of the present invention may include the inflatable devices 193 without the expansible portion 197, as shown in FIG. 9A. The inflatable devices 193 may be exposed by withdrawing the retracting sheath 201. Particularly if the inflatable devices 193 are unitary, the expansible portion 197 may not be needed. However, even if the inflatable devices 193 are separate the expansible portion 197 may be omitted.

Step 1 of FIG. 9B shows the catheter apparatus 199 in an initial state with a retractable outside sheath 201 moved as far as possible distally from a guidewire lumen tube 205. Steps 2-4 show incremental stages of retraction of the retractable outside sheath 201 to expose the one or more guidewire lumens 195 with corresponding inflatable devices 193. Steps 5-6 show incremental stages of inflation of the inflatable devices 193 into a final position with a vasculature 209 with an occlusion 211. Step 7 shows the catheter apparatus 199 in a fully deployed state. Step 8 shows a guidewire 207 inserted through a guidewire lumen 195.

FIG. 10 illustrates operation of a catheter apparatus 213 that may include shape-memory materials integrated with the one or more guidewire lumens 217. Preferably, the one or more guidewire lumens 217 may be constructed out of extruded plastic or other similar materials. Shape-memory or other expansible materials may be integrated into, surround, be contained within or reinforce the one or more guidewire lumens 217.

Step 1 of FIG. 10 shows the catheter apparatus 213 in an initial state with a retractable outside sheath 215 moved as far as possible distally from a guidewire lumen tube 215. The one or more guidewire lumens 217 may be exposed by withdrawing the retracting sheath 215 from the distal end of a catheter apparatus 213 as shown in Steps 2-6. The one or more guidewire lumens 217 may then assume a final spaced or relaxed configuration as shown in Step 7. The guidewire lumens may move outward relative to one another a desired distance and/or into contact with inner walls of a vasculature 219 with an occlusion 221. A guidewire 223 may then be threaded through the one or more guidewire lumens 217 as shown in Step 8. After completion of a procedure, the retracting sheath 215 may be advanced towards the distal end of the catheter apparatus to compress the one or more guidewire lumens 217 into a compact arrangement for removal from the vasculature 219. Alternatively, the one or more guidewire lumens 217 may be withdrawn into the distal end of the retracting sheath 215 before removal from the vasculature 219.

FIG. 11 illustrates operation of a catheter apparatus 225 with expansible devices 227 surrounding one or more guidewire lumens 229. Preferably, the expansible devices 227 are sponges or other materials that expand within the vasculature without input from a user. Each guidewire lumen 229 may have a separate expansible device 227 or multiple guidewire lumens may be incorporated into one expansible device 227.

Step 1 of FIG. 11 shows the catheter apparatus 225 in an initial state with a retractable outside sheath 231 moved as far as possible distally from a guidewire lumen tube 233. The one or more guidewire lumens 229 may be exposed by withdrawing the retracting sheath 231 from the distal end of a catheter apparatus 225 as shown in Steps 2-6. As the retracting sheath 231 is withdrawn from the expansible devices 227, the expansible devices 227 begin to expand. If the expansible devices 227 are sponges, the expansible devices 227 may absorb moisture from the vasculature to increase in volume. The one or more guidewire lumens 229 may then assume a final expanded configuration as shown in Step 7. The guidewire lumens 229 embedded with the expansible devices 227 may move outward relative to one another a desired distance and/or into contact with inner walls of a vasculature 233 with an occlusion 235. A guidewire 237 may then be threaded through the one or more guidewire lumens 229 as shown in Step 8. After completion of a procedure, the retracting sheath 231 may be advanced towards the distal end of the catheter apparatus 225 to compress the one or more guidewire lumens 229 into a compact arrangement for removal from the vasculature 233. Alternatively, the one or more guidewire lumens 229 may be withdrawn into the distal end of the retracting sheath 231 before removal from the vasculature 233. Movement of the retracting sheath 231 may compress the expansible devices 227 into a position suitable for removal from the vasculature 233. If the expansible devices 227 are sponges, the compression may force moisture out of the sponges.

Generally, after crossing a chronic total occlusion with a guidewire, the catheter apparatus may be resheathed and removed from the vasculature. The guidewire may be left in position.

One or more guidewires preferably remain in or near the longitudinal axis of the corresponding support catheter lumen. This positioning of the one or more guidewires may optimize the force of the one or more guidewires when engaged with the fibrous cap of the chronic total occlusion. Multiple eccentrically located guidewire lumens may improve the chance of success in passing one or more guidewires through a chronic total occlusion. The mass of the multi-lumen support catheter may provide additional support for the guidewire and prevents off-axis, i.e., lateral, displacement of portions of the one or more guidewires located in the guide catheter and in the vasculature. Eccentric distribution of the one or more guidewire lumens may allow engagement of multiple, eccentric sections of the fibrous cap. Embodiments of the present invention may permit simultaneous placement of multiple guidewires. Multiple guidewires may enhance available techniques such as "parallel guidewire" and "see-saw" wire.

Figure 12A:
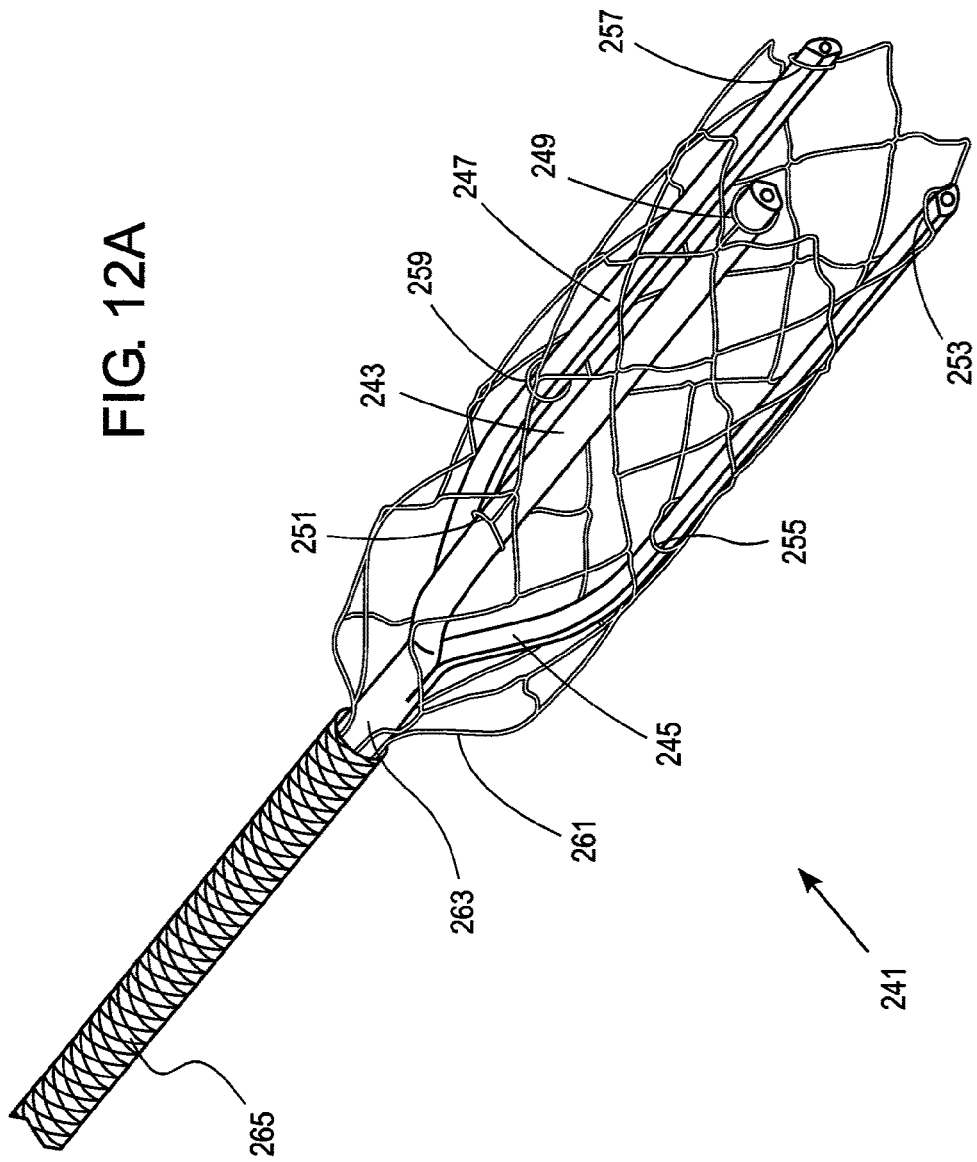
FIG. 12A is a perspective view of a loop embodiment in an expanded state.
Figure 12C:
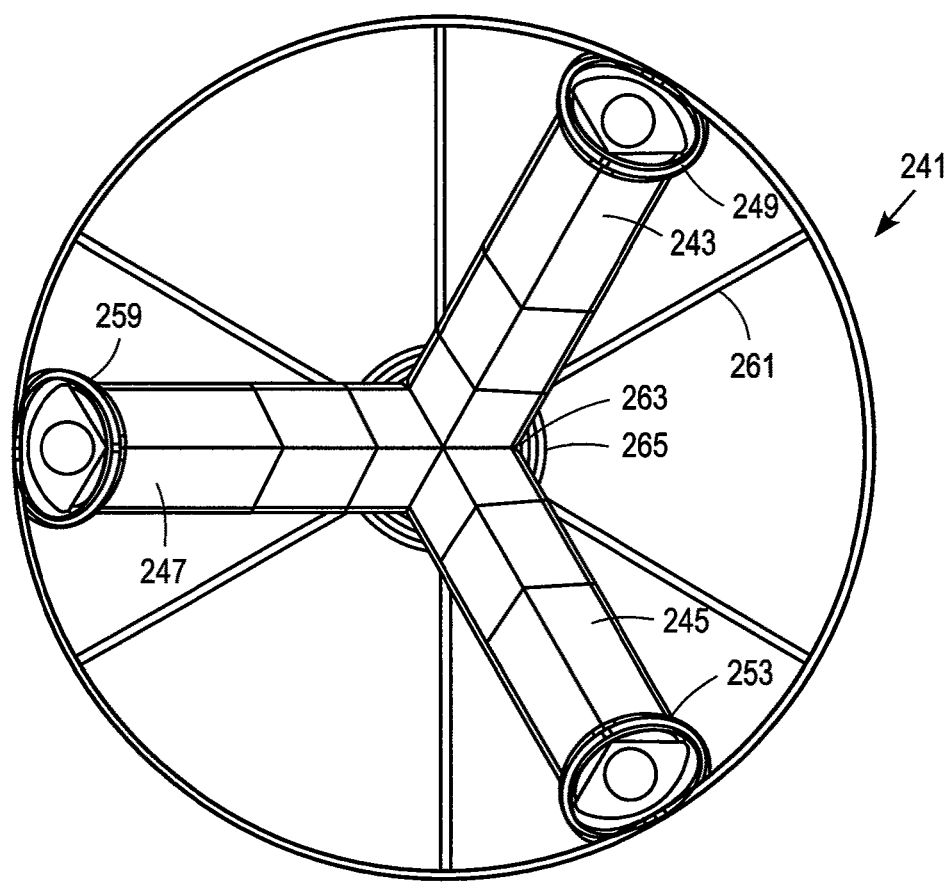
FIG. 12C is a distal end view of the loop embodiment of FIG. 12A.

FIG. 12A shows a catheter apparatus 241 with guidewire lumens 243, 245, 247 passing through loops 249, 251, 253, 255, 257, 259. The number and configuration of the loops or guidewire lumens 243, 245, 247 may be variable. Alternative numbers and configurations are possible. Guidewire lumens 243, 245, 247 may be guided into a predetermined position during expansion of an expansible support structure 261 by threading the guidewire lumens 243, 245, 247 through the inwardly projecting loops 249, 251, 253, 255, 257, 259. Loops 249, 251, 253, 255, 257, 259 may be coupled to the expansible support structure 261. FIGS. 12A-12C illustrate an embodiment of the present invention where each guidewire lumen 243, 245, 247 may pass through two loops 249, 251, 253, 255, 257, 259. Alternative embodiments may only use one loop for each guidewire lumen. Still other alternative embodiments may use three or more loops for each guidewire lumen. The operation of the loops and guidewire lumens in FIGS. 12A-12C are illustrative of the alternative embodiments. The guidewire lumens 243, 245, 247 are guided into position by passing through the loops 249, 251, 253, 255, 257, 259. The expansible support structure 261 may be coupled to a main multi-lumen shaft 263 by any conventional means such as adhesive, welding, etc. In the current embodiment of the invention, three guidewire lumens 243, 245, 247 are shown, but other numbers and configurations of lumens may be provided. A sheath 265 may hold the expansible support structure 261 in a compressed state prior to deployment of the expansible support structure 261.

FIG. 12B shows a flat projection of the expansible support structure 261 with loops 249, 251, 253, 255, 257, 259. FIGS. 12A-12C show a five closed-cell configuration. Embodiments of the present invention may include different quantities of closed-cells depending on desired applications. FIG. 12B shows a first closed cell 265, a first connector region 267, a second closed cell 269, a second connector region 271, a third closed cell 273, a third connector region 275, a fourth closed cell 277, a fourth connector region 279, and a fifth closed cell 281. In FIG. 12B, the first closed cell 265 may be at a distal end of the catheter apparatus 241 and the fifth closed cell 281 may located towards a proximal end of the catheter apparatus 241. In each closed cell, struts 283 may form a zigzag pattern to support the catheter apparatus 241. Connectors 285 residing in the first connector region 267 may connect the first closed cell 265 to the second closed cell 269 by linking strut intersections 287 on the first closed cell 267 with strut intersections 289 on the second closed cell 271. Connectors 285 may be thinner than struts 283 and the angular relationship between struts 283 and connectors 285 may change during expansion and compression of the expansible support structure 261. Similar structures and interactions may be found in and between the remaining closed cells.

Loops 249, 251, 253, 255, 257, 259 may be located at strut intersections 291. Loops 249, 251, 253, 255, 257, 259 may be coupled to the strut intersections 291 by loop supports 293. Loop supports 293 may be tapered to reduce stress on the apparatus. Struts 283 may also be tapered to reduce stress on the apparatus. The loop supports 293 may be positioned at other locations along the struts 283 or connectors 285 if desired. Loops 249, 251, 253, 255, 257, 259 and inner shape cutouts may be circular, oval, oblong or any additional shapes to allow the guidewire lumens 243, 245, 247 to slide within the loops 249, 251, 253, 255, 257, 259. Shapes other than circles may be beneficial when the loops 249, 251, 253, 255, 257, 259 lie at an angle other than perpendicular to the cylindrical plane of the expansible support structure 261. Loops 249, 251, 253, 255, 257, 259 may be shaped to correspond to guidewire lumens 243, 245, 247 and allow the guidewire lumens 243, 245, 247 to slide through the loop openings.

Each guidewire lumen 243, 245, 247 may pass through two loops in the embodiment of FIGS. 12A-12C. For example, guidewire lumen 243 may pass through loops 249 and 251, guidewire lumen 245 may pass through loops 253 and 255, and guidewire lumen 247 may pass through loops 257 and 259. Passing the guidewire lumens 243, 245, 247 through the loops 249, 251, 253, 255, 257, 259 may position the guidewire lumens 243, 245, 247 in a desired position within the expansible support structure 261. As indicated above, other numbers and configurations of loops are possible. To prevent twisting and damage to the guidewire lumens 243, 245, 247, the loops 249, 251, 253, 255, 257, 259 for each guidewire lumen are preferably located on every other closed cell. As shown in FIG. 12B, the loops 249, 251, 253, 255, 257, 259 are located on the first closed cell 265 and the third closed cell 273. The loops 249, 251, 253, 255, 257, 259 may also be located on, for example, the second closed cell 269 and the fourth closed cell 277. If additional loops are present, then the loops may be located on closed cells separated by one closed cell. This alternating structure may prevent twisting during expansion and compression of the expansible support structure 261 that may damage or misalign the guidewire lumens 243, 245, 247. Preferably, no loops 249, 251, 253, 255, 257, 259 may be located on the fifth or proximal closed cell 281. The fifth closed cell 281 may be adhered to the main tri-lumen shaft 263. Thus, the fifth closed cell 281 may not fully expand during expansion of the expansible support structure 261 and may not be appropriate for holding loops 249, 251, 253, 255, 257, 259. Similarly, the fourth closed cell 277 may not fully expand and may also not be suitable for holding loops.

The expansible support structure 261, the guidewire lumens 243, 245, 247, and the loops 249, 251, 253, 255, 257, 259 may initially be in a compressed state within a sheath 265 as described in previous embodiments. The sheath 265 may hold the expansible support structure 261 in a compressed state. The sheath 265 may include a radiopaque marker at a distal end of the sheath 265 or another known location along the sheath 265. The radiopaque marker may provide an indication of how much of the expansible support structure 261 is covered by the sheath 265. This may allow for partial withdrawal of the sheath 265.

The expansible support structure 261 may be made of nitinol or another shape-memory material. The loop connectors 293 may also be made of nitinol or another shape-memory material. The loop connectors 293 may be set to project inwardly from the cylindrical plane of the expansible support structure 261 at a given angle. The angle may be any angle, but is preferably approximately 30 degrees inward from the cylindrical plane. The angle or the length of the loop connectors 293 or both may be varied to create various positions of the guidewire lumens 243, 245, 247 within the expansible support structure 261. The loops 249, 251 corresponding to a guidewire lumen 243 may project in opposite directions, for example, loop 249 may project in a distal direction, and loop 251 may project in a proximal direction.

When the sheath 265 is withdrawn from around the expansible support structure 261, the expansible support structure 261 may expand to an expanded state. The sheath 265 may be partially or completely withdrawn from the expansible support structure 261. During expansion of the expansible support structure 261, the loops 249, 251, 253, 255, 257, 259 may project inward from the cylindrical plane of the expansible support structure 261 to hold the guidewire lumens 243, 245, 247 in a predetermined position within the expansible support structure 261. The guidewire lumens 243, 245, 247 may remain within the loops 249, 251, 253, 255, 257, 259 during expansion and compression of the expansible support structure 261. Also during expansion, the angle of the connectors 285 relative to the closed cells may change. Placing the loops 249, 251, 253, 255, 257, 259 on closed cells separated by one closed cell may keep the guidewire lumens 243, 245, 247 from twisting. As the expansible support structure 261 expands, the guidewire lumens 243, 245, 247 may diverge into predetermined positions. The expanded catheter apparatus 241 may not block the vasculature.

Upon completion of a procedure, the expansible support structure 261 may be compressed and withdrawn from the vasculature. The sheath 265 may be slid distally over the expansible support structure 261. Preferably, no parts of the catheter apparatus 241 extend outside of the cylindrical plane of the compressed expansible support structure 261 in the compressed state to facilitate withdrawal of the catheter apparatus 241.

Figure 13:
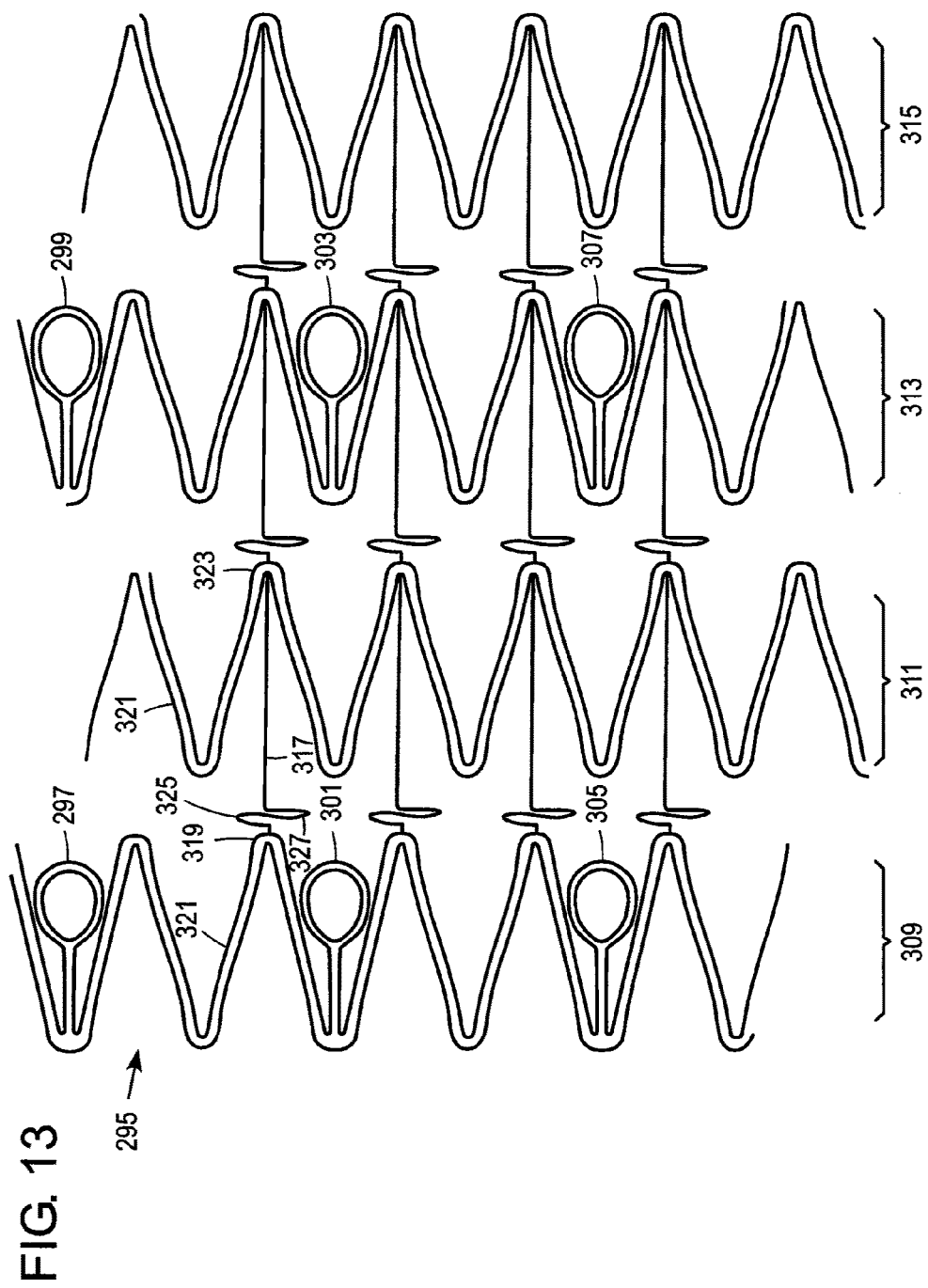
FIG. 13 is an unwrapped view of another loop embodiment where loops may be located on any closed cell.

FIG. 13 shows another loop embodiment of an expansible structure 295. In contrast to the loop embodiment 241 of FIGS. 12A-12C, the loop embodiment of the expansible structure 295 of FIG. 13 may have loops 297, 299, 301, 303, 305, 307 attached on any of closed cell 309, 311, 313, 315. The operation of the apparatus of the loop embodiment of the expansible structure 295 is similar to the operation of the loop embodiment 241 of FIGS. 12A-12C.

To prevent twisting and damage to guidewire lumens 243, 245, 247, connecting members 317 may couple connection points 319 of struts 321 on a closed cell, such as 309, to connection points 323 of struts 321 on an adjacent closed cell, such as 311. The connection points 319, 323 are preferably both distal or both proximal relative to the distal end of the catheter apparatus 295. The number and configuration of the connecting members 317 may be variable. The connecting members 317 may have an upward bend 325 and a downward bend 327. The bends 325, 327 prevent twisting and damage to the guidewire lumens 243, 245, 247 during expansion and contraction of the expansible structure 295. During expansion and contraction of the expansible structure 295, the upward bend 325 and the downward bend 327 cancel and lateral movement of the loops 297, 299, 301, 303, 305, 307.

The connecting members 317 of the expansible structure 295 may allow loops on each closed cell 309, 311, 313, 315. Loops 297, 299, 301, 303, 305, 307 do not need to be on every other closed cell 309, 311, 313, 315. The embodiment of FIG. 13 may provide for flexibility of the expansible structure 295 and may facilitate expansion and contraction during deployment and removal.

The invention also includes embodiments of a catheter apparatus having translating lumens. In particular, one or more smaller lumen catheters pass through the lumen of the catheter apparatus. These lumen catheters, in various quantities, may be individually, jointly, or a combination thereof movable such that the lumen catheters are capable of telescoping. For example, the lumen catheters can be advanced individually or collectively beyond the distal end of the catheter apparatus. The lumen catheters can be advanced and retracted as desired in an effort to cross a lesion, for example. The lumen catheters are configured to allow passage of one or more guidewires. Any of the lumens of any of the catheter embodiments above may be configured to allow passage of these lumen catheters. Thus, the translating lumen catheters may be used in any of the embodiments described above.

The lumen catheters may be shafts configured for passing over the guidewire. In certain embodiments, the lumen catheters may be constructed as shafts with either a circular, oval, or rectangular shape. Other shapes are possible depending on particular uses. Furthermore, each lumen catheter may be individually movable and advanceable beyond the distal end of the catheter apparatus as well as retractable into the catheter apparatus. The lumen catheters may be capable of extending beyond the distal end of the catheter apparatus and retracting into the catheter apparatus. Each of the lumen catheters may be capable of being advanceable and rectractable, for example, approximately 1 to 3 inches, beyond the distal end of the shaft of the catheter apparatus. In one embodiment, an actuator may control movement of the one or more lumen catheters.

This embodiment may include a catheter apparatus including an outer shaft (such as a sheath) having a lumen, a main catheter shaft having a lumen, one or more lumen catheters configured for passing over one or more guidewires and a scaffold structure whereby the scaffold structure is attached to the inner shaft, and whereby the inner shaft and one or more lumen catheters telescope independently of each other. The scaffold may be configured to be non-occluding, allowing blood to flow through. Features of the present invention also include expansion or activation of a distal tip for creating a scaffold structure. In certain embodiments, the outer shaft (e.g. sheath), main catheter shaft and lumen catheters may be slideably operable independently of each other.

The lumen catheters may advance and/or retract in any combination of patterns and/or in unison. The movement may be controlled on an individual lumen catheter basis or movement relative to other, one or more of the other lumen catheters and/or the catheter. Thus, the lumen catheters may be used to attack an occlusion at more than one position. For example, in one embodiment, two lumen catheters may be individually advanced to attack an occlusion at two different positions.

FIG. 14A-D show catheter 335 having lumen catheters 337, 339 and 341 and its operation. The lumen catheters 337, 339 and 341 pass through one or more lumens in catheter 335. The lumen catheters 337, 339 and 341 may be movable. Thus, lumen catheters 337, 339 and 341 may be capable of advancing beyond the distal end of the catheter apparatus and capable of retracting into the catheter apparatus. The lumen catheters may be individually or jointly movable. The lumen catheters may also be operably linked to an actuator. Operation of the actuator may result in advancement/retraction of one or more lumen catheters. The actuator may be configured so that in mode one more the lumens move jointly and while moving individually (separately) in another mode. In certain embodiments, the lumen catheters may be directly attached to the actuator.

Figure 14A:
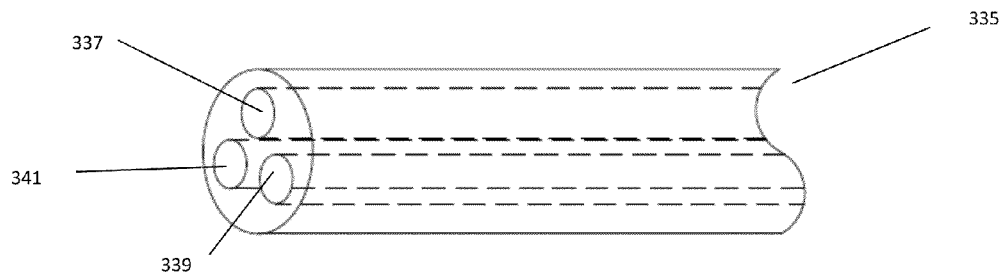
Figure 14B:
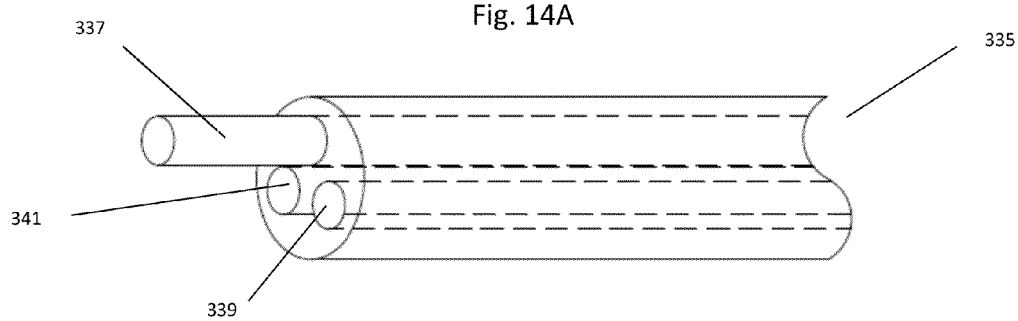
Figure 14C:
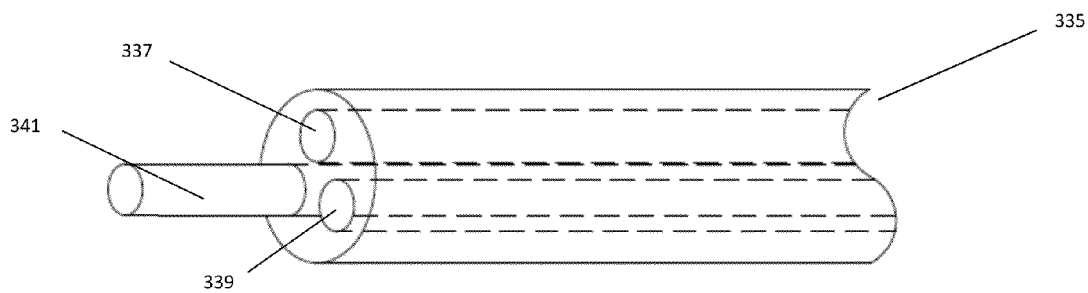
Figure 14D:
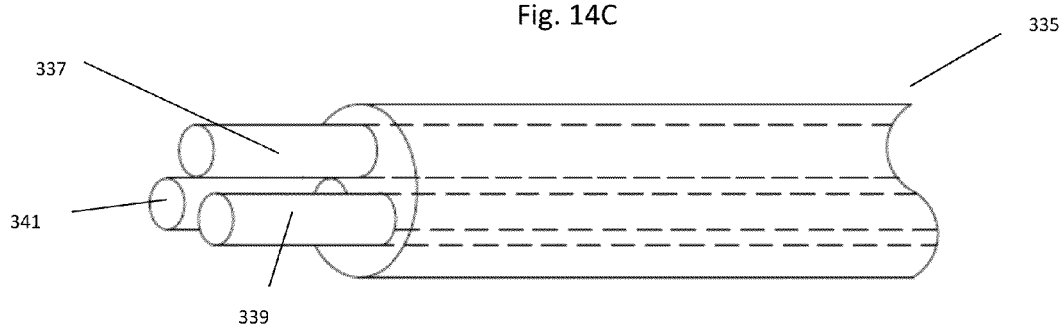

FIG. 14A shows the lumen catheters 337, 339 and 341 in their unextended position inside the distal end of catheter 335. In that position, the distal end of the lumen catheters 337, 339 and 341 is approximately flush with the distal end of catheter 335. Catheter 335 may be configured to be a hollow tube. Alternatively, catheter 335 may be a solid tube with a lumen for each lumen catheter 337, 339, and 341. The lumens may be distributed approximately equidistant from each other. FIG. 14B shows the telescoping of lumen catheter 337. As shown in FIG. 14B, lumen catheter 337 advances from the distal end of catheter 335. Lumen catheters 339 and 341 may remain in their retracted position or they may telescope jointly or individually. FIG. 14C shows lumen catheter 341 in its extended position. In certain embodiments, lumen catheter 341 may extend between about 1 and about 3 inches beyond the distal end of the catheter 335. FIG. 14D shows lumen catheters 337, 339, and 341 in their extended position telescoping from the distal end of the catheter 335. The lumen catheters 337, 339 and 341 may be configured to allow passage of one or more guidewire through each lumen catheter.

Figure 14E:
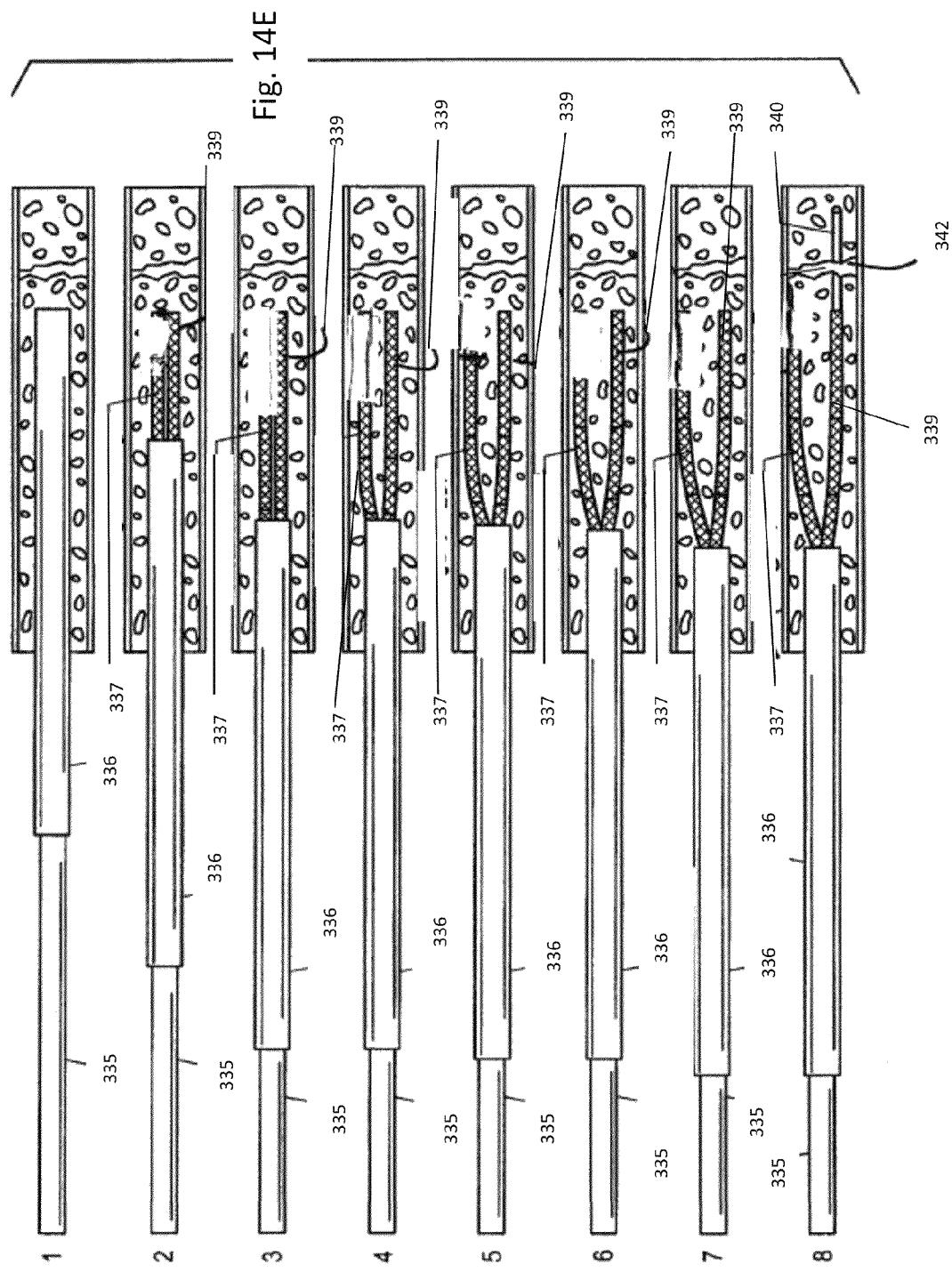

FIG. 14E illustrates operation a catheter apparatus 335 with lumen catheters 337 and 339. The lumen catheters 337 and 339 may be jointly or separately movable. An actuator (not shown) may control movement of the lumen catheters 337 and 339. The lumen catheters 337 and 339 are configured for passage of one or more guidewires. While only two lumen catheters are shown, it should be understood that the number of lumen catheters may vary. The lumen catheters have a lumen therethrough. A guidewire, such as guidewire 340, may pass through the lumen of the lumen catheter.

Step 1 of FIG. 14E shows the catheter apparatus 335 in an initial state with optional retractable outside sheath 336 covering the distal end of the catheter apparatus 335. It should be understood that in alternate embodiments, catheter 335 does not have outside sheath 336. The distal end of the catheter apparatus 335 may be exposed by withdrawing the retracting sheath from the distal end of the catheter apparatus as shown in Step 2. As the catheter apparatus is positioned, lumen catheter 337 and 339 are individually advanced and guidewires 338 and 340 may be advanced beyond the distal end of the lumen catheters. The one or more lumen catheters 337 and 339 may then assume a final spaced or relaxed configuration. The one or more lumen catheters 337 and 339 may move outward relative to one another a desired distance and/or into contact with inner walls of a vasculature with an occlusion 340. The lumen catheters 337 and 339 may assume a final spaced or relaxed configuration as shown in Step 7. As shown in steps 2 to 7, the guidewires are still inside the lumen catheter 337 and 339. A guidewire 340 may then be threaded through the one or more lumen catheters (e.g. lumen catheter 339) as shown in Step 8 to pass through occlusion 342. After completion of a procedure, the retracting sheath 336 may be advanced towards the distal end of the catheter apparatus to compress the one or more guidewire lumen catheters 337 and 339 into a compact arrangement for removal from the vasculature. Alternatively, the one or more lumen catheters 337 and 339 may be withdrawn into the distal end of the retracting sheath 336 before removal from the vasculature.

The guidewires can be advanced regardless of the position of the lumen catheters. The guidewires 338 and 340 of the catheter apparatus may be moved into closer contact with the occlusion 342. In one embodiment, the guidewires are advanced when the one or more lumen catheters 337 and 339 assume a final spaced or relaxed configuration. The guidewires 338 and 340 may move outward relative to one another a desired distance and/or into contact with inner walls of a vasculature with an occlusion 340. In one embodiment, the guidewires 338 and 340 may be advanced before the one or more lumen catheters 337 and 339 are in contact with a vasculature. In another embodiment, the guidewires 338 and 340 may not be advanced until the one or more lumen catheters 337 and 339 are in contact with a vasculature.

The lumen catheters 337, 339 and 341 may be surrounded by an expandable support structure. In one embodiment, a single expandable support structure may surround all of the lumen catheters. One or more expandable support structures are contemplated. Thus, in certain embodiment, each of the lumen catheters may be surrounded by an expandable support structure that only surrounds that lumen catheter.

The expandable support structure may be attached to one or more of the lumen catheters such that advancement of the lumen catheters results in expansion of the expandable support structure. Any of the expandable support structures described herein (such as e.g. scaffolds) may be used. The lumen catheters may also be operably linked to an actuator. The actuator may be configured so that in one embodiment one or more the lumens are capable of moving jointly in one mode, capable of moving individually (separately) in another mode and/or any combination of individual and joint movement. In certain embodiments, the lumens may be directly attached to an actuator.

FIGS. 15A-C show the distal end of a catheter 343 having lumen catheters 345, 347 and 349 and expandable support structure 351. The expandable support structure 351 surrounds the lumen catheters 345, 347, and 349. The expandable support structure may surround all of the lumen catheters together. The expandable support structure may be retractable into catheter 343, as described in more detail above. Alternatively, a sheath as described above may cover the expansible support structure 351. The catheter 343 may be a hollow tube, as described in more detail above. Alternatively, catheter 343 may be a solid tube with at least a lumen for each of the lumen catheters.

FIG. 15A shows the distal end of a catheter 343 (not shown) having lumen catheters 345, 347, 349, and expansible support structure 351 with the expansible support structure in its expanded state. Any number of lumen catheters may be used. Each lumen catheter 345, 347, and 349 has a lumen 354 extending therethrough and the lumen is configured for passing a guidewire. Guidewire 355 is shown passing through lumen catheter 347. The guidewire 355 may also be advanceable through the lumen catheter 347. Alternatively, each lumen catheter may have one or more lumen provided through each lumen catheter. The expansible support structure 351 may have one or more loops 353. Each of the lumen catheters may be in held in position by the one or more loops 353. The at least one of the one or more loops 353 may be located towards the distal end of expansible support structure 351 with a lumen catheter passing therethough. The lumen catheters 345, 347 and 349 may be individually or jointly moveable. In one embodiment, the lumen catheters 345, 347 and 349 may telescope beyond the distal end of the expansible support structure 351. The distal end of lumen catheters 345, 347 and 349 may pass through loops 353 on the distal end of expansible support structure 351. The distal end of lumen catheter such as e.g. lumen catheter 357 may be configured to be advanceable beyond the distal of expansible support structure 351.

FIG. 15B is a distal end view of catheter 343 with lumen catheters 345, 347, and 349. Each of the lumen catheters 345, 347, and 349 has one or more lumens through which guidewires 355 may pass. Expansible support structure 351 is shown surrounding lumen catheter 345, 347, and 349. As shown in FIG. 15C, catheter has one lumen configured for passage of each of the lumen catheters.

FIG. 15C illustrates the operation of catheter 343 of FIG. 15A and FIG. 15B. In particular, this figure illustrates how in certain embodiments of the invention illustrate how the guidewires advance. This figure also illustrates how the telescoping lumen catheters serve to follow the guidewire and may provide support to the guidewire. Similar operational procedures may be used for other embodiments described herein. Step 1 of FIG. 15C shows catheter 343 with optional retractable outside sheath 356 (not shown) moved back distally from the catheter 343 such that expansible scaffold 351 is partially exposed. Steps 2 to 4 show further incremental stages of retraction of the retractable outside sheath 356. As the retractable outside sheath 356 is retracted back over the catheter 343, the expansible support structure 351, which surrounds lumen catheters 345, 347, and 349, is incrementally exposed and allowed to expand. As the expansible support structure 351 expands the lumen catheters 345, 347 and 349 separate and are held in a desired position by the shape-memory allow materials or by coupling to the expansible portion 357. Step 4 shows the expansible support structure 351 in a fully deployed state. Steps 11 and 12 show lumen catheters 345, 347 and 349 with the expansible support structure 351 in a fully deployed state. At any stage of the expansion, the lumen catheters 345, 347 and 349 may be advanced to telescope beyond the distal end of the expansible support structure 351 or retracted. Thus, for example, as shown in Steps 6 to 12 of FIG. 15C, lumen catheter 347 may be advanced to telescope beyond the distal end of expansible support structure 351 or retracted. Furthermore, guidewire 355 may also be advanced to telescope and/or retracted at any stage of the expansion. Thus, as shown in steps 8 to 12, guidewire 355 may be advanced beyond the distal end of lumen catheter 347.

In another embodiment of a catheter apparatus according to the invention, the one or more lumen catheters surround the main catheter shaft rather than passing through a lumen in the main catheter shaft. The scaffold is disposed on or attached to towards the distal of the catheter shaft. The main catheter shaft may have one or more lumens. Alternatively, the main catheter shaft may not have a lumen. FIG. 16A to C show the distal end of catheter 361 having main catheter shaft 373, expansible scaffold 369 and lumen catheters 363, 365, and 367. Catheter 361 may have lumens through which lumen catheters 363, 365, and 367 may pass. Alternatively, catheter 361 may not have a lumen. FIG. 16A shows lumen catheters 363, 365, and 367 of catheter 361 (not shown). The number and arrangement of lumen catheters can vary depending on the contemplated use. Each of the lumen catheters 363, 365 and 367 has a lumen through which a guidewire may pass. As shown in FIG. 16A, the lumen catheters 363, 365, and 367 may expand outwardly towards the distal end. FIG. 16A also shows end views of the distal and proximal end of the lumen catheters 363, 365, and 367 including their lumens. FIG. 16B shows expansible scaffold 369 in its expanded state. The scaffold 369 is disposed or attached towards the distal end of main catheter shaft 373. The scaffold 369 may be disposed on or attached to the distal end of main catheter shaft. The scaffold 369 includes cells 375 and inward facing loops 371. Each cell is approximately hexagonal and has expansible S-shaped (zig-zag) connectors 377 on two opposing sides of the hexagon. The configuration and arrangement of each cell, including the connectors, may vary. For example, the connectors may be approximately FIG. 8 shaped. The inward facing loops 371 are configured for passing over lumen catheters 363, 365, and 367. FIG. 16B also shows a distal end view of the scaffold 369 with loops 371 visible and a proximal end view the main catheter body. As shown in FIG. 16C, main catheter shaft 373 may be surrounded by lumen catheters 363, 365 and 367. FIG. 16C shows the distal end of catheter 361. The distal end view shows lumen catheters 363, 365 and 367 passing through inward facing loops of scaffold 369. FIG. 16C also shows the proximal end view of catheter 361. In the proximal end view, main catheter body 373 is surrounded by lumen catheters 363, 365, and 367. This embodiment of the device can achieve a lower overall profile and greater flexibility than when the scaffold is attached to the catheter. Furthermore, the configuration of this device allows for additional space for the telescoping lumens to move.

FIG. 17A is a perspective view of expansible scaffold 391 in its expanded state, which may be used in a catheter apparatus of the invention. Scaffold 391 includes cells 393. Each cell is approximately hexagonal and has expansible S-shaped (zig-zag) connectors 395 on two opposing sides of the hexagon. In one embodiment, these S-shaped (zig-zag) connectors are approximately parallel to an axis passing through the center of the scaffold from the distal to the proximal end. The scaffold also includes inward projecting loops 397. The loops are configured for passing a lumen catheter. The number and configuration of the loops and cells, including the connectors, may vary. FIG. 17B shows a flat projection of expansible scaffold 391 with hexagonal cells 393, S-shaped (zig-zag) connectors 395 and loops 397.

FIG. 18A to C show another embodiment of a catheter apparatus in accordance with the invention. Catheter apparatus 399 utilizes scaffold 391 described above. As shown in FIG. 18, catheter apparatus 399 includes main catheter body 405, scaffold 391 and lumens 407, 409 and 411. Lumens 407, 409 and 411 extend through the main catheter body beyond the distal end of the catheter body. As discussed above, scaffold 391 includes hexagonal cells 393, S-shaped (zig-zag) connectors 395 and loops 397. Lumens 407, 409 and 411 may pass through loops 397. Loops 397 of the scaffold 391 may position the lumens 407, 409 and 411 on the inside of the scaffold 391. The catheter apparatus may include sheath 401, which has a lumen through which main catheter body 405 may pass. The distal end of sheath 401 may have a two parallel longitudinal axes running from opposing sides of the lumen of sheath 401. The closer longitudinal axis passes through the distal tip of sheath 401 and the further longitudinal axis passes through the opposite end of the sheath 401. The distal end of the sheath 401 may be tapered towards the closer longitudinal axis. This configuration aids in tracking of the catheter tip over a guidewire. Alternatively, the distal tip of the sheath 401 may be tapered, beveled, round or combinations thereof. The sheath 401 may include position detection marker 403 towards the distal end of the sheath. The detection marker 403 may be a radio-opaque marker band. The proximal end of scaffold 391 is disposed toward or on the distal end of the main catheter body 405. The proximal end of the scaffold 391 may be physically attached to main catheter body 405. The proximal end of the scaffold may be held in place by a biologically acceptable glue or a fitting 413. When used as part of the apparatus, fitting 413 slides over the proximal end of the scaffold and holds it in place. As with the other embodiments, this embodiment of the catheter apparatus may be configured to allow passage of translating lumen catheters, which may telescope.

FIG. 18B shows a cross-sectional view taken at Section A-A in FIG. 18A. This cross section view shows the outer sheath 401 surrounding the main catheter body 405. Lumens 407, 409 and 411 are also visible. In the center of the lumens is a small wire running the length of the catheter body. This wire prevents the lumen from stretching or compressing while maintaining flexibility. In addition, FIG. 18C shows an end view of the distal end of catheter apparatus 399. The end view shows scaffold 391, lumens 407, 409 and 411 extending beyond main catheter body 405 and passing through the scaffold 397.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

What is claimed is:
1. A catheter apparatus comprising:
   a main catheter shaft;
   one or more telescoping lumen catheters, each telescoping lumen catheter configured for passing over one or more guidewire; each lumen catheter capable of telescoping in and out from a distal end of the main catheter shaft; and
   a non-implantable, removable expansible support structure coupled to the distal end of the main catheter shaft, the expansible support structure configured so that each telescoping lumen catheter can telescope in and out of the expansible support structure,
   wherein the expansible support structure is configured to be insertable and removable in a procedure, wherein the expansible support structure has one or more loops each corresponding to one or more of the one or more telescoping lumen catheters and wherein each of the one or more telescoping lumen catheters are threaded through the corresponding one or more loops.

2. The apparatus of claim 1, wherein the main catheter shaft further comprises one or more telescoping lumen catheter shafts corresponding to each of the one or more telescoping lumen catheters.

3. The apparatus of claim 2, wherein the one or more telescoping lumen catheters pass through the one or more telescoping lumen catheter shafts.

4. The apparatus of claim 1, wherein the one or more telescoping lumen catheters are coupled to the expansible support structure.

5. The apparatus of claim 1, wherein the expansible support structure is capable of surrounding the one or more telescoping lumen catheters.

6. The apparatus of claim 5, wherein the one or more loops are inward facing loops.

7. The apparatus of claim 6, wherein the one or more inward facing loops are coupled to the expansible support structure by loop connections.

8. The apparatus of claim 1, wherein the expansible support structure comprises closed cells.

9. The apparatus of claim 8, wherein the closed cells are in a hexagonal configuration with expansible S-shaped connectors on two opposing sides of the hexagon.

10. The apparatus of claim 1 further comprising a retractable sheath covering at least a portion of the expansible support structure of the main catheter shaft, wherein the main catheter shaft has a distal portion, and wherein retracting the sheath from the distal portion of the shaft allows the expansible support structure to expand.

11. The apparatus of claim 10, wherein the retractable sheath may be advanced around the expansible support structure to compress the expansible support structure.

12. The apparatus of claim 1, wherein the one or more telescoping lumen catheters are capable of separately telescoping in and out of the main catheter shaft.

13. The apparatus of claim 1 further comprising an actuator.

14. The apparatus of claim 13, wherein operation of the actuator controls movement of the one or more telescoping lumen catheters.

15. The apparatus of claim 1, wherein the expansible support structure comprises a shape memory alloy.

16. The apparatus of claim 1, wherein the one or more telescoping lumen catheters surround the main catheter shaft and wherein the distal end of each of the one or more telescoping lumen catheters is coupled to the support structure.

17. The catheter apparatus of claim 1, wherein the expansible support structure is a scaffold.

18. The catheter apparatus of claim 1, wherein the expansible support structure has a distal end and wherein the expansible support structure configured so that each telescoping lumen catheter can telescope in and out of the distal end of the expansible support structure.

19. The catheter apparatus of claim 1, wherein the expansible support structure is self-expandable.

* * * * *